(12) United States Patent
Kolczewski et al.

(10) Patent No.: US 8,063,098 B2
(45) Date of Patent: Nov. 22, 2011

(54) GLYT1 RECEPTOR ANTAGONISTS

(75) Inventors: Sabine Kolczewski, Loerrach (DE); Robert Narquizian, Saint Louis (FR); Emmanuel Pinard, Linsdorf (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 280 days.

(21) Appl. No.: 12/541,202

(22) Filed: Aug. 14, 2009

(65) Prior Publication Data

US 2010/0048531 A1 Feb. 25, 2010

(30) Foreign Application Priority Data

Aug. 20, 2008 (EP) .................................. 08162652

(51) Int. Cl.
*A61K 31/40* (2006.01)
*C07D 207/04* (2006.01)

(52) U.S. Cl. ........ 514/428; 548/566; 548/567; 544/106; 514/231.2; 514/408

(58) Field of Classification Search .................. 548/566, 548/567; 544/106; 514/231.2, 408, 428
See application file for complete search history.

(56) References Cited

U.S. PATENT DOCUMENTS 7,126,027 B2 * 10/2006 Morphy et al. ............... 564/177

FOREIGN PATENT DOCUMENTS

| WO | WO 03/010132 | 2/2003 |
| WO | WO 2006/067414 | 6/2006 |
| WO | WO 2006/067437 | 6/2006 |
| WO | WO 2007/060484 | 5/2007 |

OTHER PUBLICATIONS

Lewis D.A. & Lieberman J.A., Neuron. vol. 28, pp. 325-334 (2000).
Vandenberg R. J. & Aubrey K. R., Exp. Opin. Ther. Targets vol. 5(4) pp. 507-518 (2001).
Nakazato A. & Okuyama S., Exp. Opin. Ther. Patents vol. 10(1) pp. 75-98 (2000).
Sharma T., Br. J. Psychiatry, vol. 174 (Suppl. 38) pp. 44-51 (1999).
Javitt D. C. et al., Biol. Psychiatry, vol. 45 pp. 668-679 (1999).
Mohn A. R., Cell vol. 98 pp. 427-436 (1999).
Bliss, T. V. & Collingridge G. L., Nature, vol. 361 pp. 31-39 (1993).
Tang J. P. et al., Nature, vol. 401, pp. 63-69 (1999).
Gainetdinov R. R. et al., Trends in Pharm. Sci. vol. 23(8) pp. 367-373 (2002).
Lopez-Corcuera B, et al., Mol. Mem. Biol. vol. 18 pp. 13-20 (2001).
Bergeron R. et al., Proc. Natl. Acad. Sci. USA vol. 95, pp. 15730-15734 (1998).
Chen et al., J. Neurophysiol. vol. 89(2) pp. 691-703 (2003).
Armer et al., Exp. Opin. Ther. Patents, vol. 11(4) pp. 563-572 (2001).
Pralong et al., Prog. Neurobiol. vol. 67 pp. 173-202 (2002).
Carlsson M. L., Neural, Trans. pp. 525-535 (1998).

* cited by examiner

*Primary Examiner* — Golam M Shameem
(74) *Attorney, Agent, or Firm* — George W. Johnston; Patricia S. Rocha-Tramaloni; Kimberly J. Prior

(57) ABSTRACT

The present invention relates to a compound of formula I

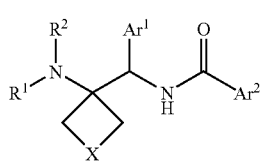

wherein
$R^1$, $R^2$, X, $Ar^1$ and $Ar^2$ are as defined herein and to pharmaceutically acceptable acid addition salts, to a racemic mixtures, or to their corresponding enantiomers and/or optical isomers thereof. Compounds of the invention are good inhibitors of the glycine transporter 1 (GlyT-1), and have a good selectivity to glycine transporter 2 (GlyT-2) inhibitors.

11 Claims, No Drawings

GLYT1 RECEPTOR ANTAGONISTS

PRIORITY TO RELATED APPLICATION(S)

This application claims the benefit of European Patent Application No. 08162652.5, filed Aug. 20, 2008, which is hereby incorporated by reference in its entirety.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, Neuron, 28:325-33, 2000). For decades research has focused on the "dopaminergic hyperactivity" hypothesis which has led to therapeutic interventions involving blockade of the dopaminergic system (Vandenberg R J and Aubrey K R., Exp. Opin. Ther. Targets, 5(4): 507-518, 2001: Nakazato A and Okuyama S, et al., Exp. Opin. Ther. Patents, 10(1): 75-98, 2000). This pharmacological approach poorly address negative and cognitive symptoms which are the redictors of functional outcome (Sharma T., Br. J. Psychiatry, 174(suppl. 28). 44-51, 1999).

A complementary model of schizophrenia was proposed in the mid-1960s based upon the psychotomimetic action caused by the blockade of the glutamate system by compounds like phencyclidine (PCP) and related agents (ketamine) which are non-competitive NMDA receptor antagonists. Interestingly, in healthy volunteers, PCP-induced psychotomimetic action incorporates positive and negative symptoms as well as cognitive dysfunction, thus closely resembling schizophrenia in patients (Javitt D C et al., Biol. Psychiatry, 45: 668-679, 1999). Furthermore transgenic mice expressing reduced levels of the NMDAR1 subunit display behavioral abnormalities similar to those observed in pharmacologically induced models of schizophrenia, supporting a model in which reduced NMDA receptor activity results in schizophrenia-like behavior (Mohn A R et al., Cell, 98: 427-236, 1999).

Glutamate neurotransmission, in particular NMDA receptor activity, plays a critical role in synaptic plasticity, learning and memory, such that NMDA receptors appear to serve as a graded switch for gating the threshold of synaptic plasticity and memory formation (Wiley, N.Y.; Bliss TV and Collingridge G L, Nature, 361: 31-39, 1993). Transgenic mice over-expressing the NMDA NR2B subunit exhibit enhanced synaptic plasticity and superior ability in learning and memory (Tang J P et al., Natur. 401-63-69, 1999).

Thus, if a glutamate deficit is implicate in the pathophysiology of schizophrenia, enhancing glutamate transmission, in particular via NMDA receptor activation, would be predicted to produce both anti-psychotic and cognitive enhancing effects.

The amino acid glycine is known to have at least two important functions in the CNS. It acts as an inhibitory amino acid, binding to strychnine sensitive glycine receptors, and it also influences excitatory activity, acting as an essential co-agonist with glutamate for N-methyl-D-aspartate (NMDA) receptor function. While glutamate is released in an activity-dependent manner from synaptic terminals, glycine is apparently present at a more constant level and seems to modulate/control the receptor for its response to glutamate.

One of the most effective ways to control synaptic concentrations of neurotransmitter is to influence their re-uptake at the synapses. Neurotransmitter transporters act by removing neurotransmitters from the extracellular space, and can control their extracellular lifetime and thereby modulate the magnitude of the synaptic transmission (Gainetdinov R R et al, Trends in Pharm. Sci., 23(8): 367-373, 2002).

Glycine transporters, which form part of the sodium and chloride family of neurotransmitter transporters, play an important role in the termination of post-synaptic glycinergic actions and maintenance of low extracellular glycine concentration by re-uptake or glycine into presynaptic nerve terminals and surrounding fine glial processes.

Two distinct glycine transporter genes have been cloned (GlyT-1 and GlyT-2) from mammalian brain, which give rise to two transporters with ~50% amino acid sequence homology. GlyT-1 presents four isoforms arising from alternative splicing and alternative promoter usage (1a, 1b, 1c and 1d). Only two of these isoforms have been found in rodent brain (GlyT-1a and GlyT-1b). GlyT-2 also presents some degree of heterogeneity. Two GlyT-2 isoforms (2a and 2b) have been identified in rodent brains. GlyT-1 is known to be located in CNS and in peripheral tissues, whereas GlyT-2 is specific to the CNS. GlyT-1 has a predominantly glial distribution and is found not only in areas corresponding to strychnine sensitive glycine receptors but also outside these areas, where it has been postulated to be involved in modulation of NMDA receptor function (Lopez-Corcuera B et al., Mol. Mem. Biol., 18: 13-20, 2001). Thus, one strategy to enhance NMDA receptor activity is to elevate the glycine concentration in the local microenvironment of synaptic NMDA receptors by inhibition of GlyT-1 transporter (Bergereon R. et al., Proc. Natl. Acad. Sci. USA, 95: 15730-15734, 1998; Chen L. et al., J. Neurophysiol., 89(2): 691-703, 2003).

Glycine transporter inhibitors are suitable for the treatment of neurological and neuropsychiatric disorders. The majority of diseases states implicated are psychoses, schizophrenia (Armer R E and Miller D J, Exp. Opin. Ther. Patents, 11 (4): 563-572, 2001), psychotic mood disorders such as severe major depressive disorder, mood disorders associated with psychotic disorders such as acute mania or depression, associated with bipolar disorders and mood disorders, associated with schizophrenia, Pralong E T et al., Prog. Neurobiol., 67: 173-202, 2002), autistic disorders (Carlsson M L, J. Neural Trans,. 105: 525-535, 1998), cognitive disorders such as dementias, including age related dementia and senile dementia of the Alzheimer type, memory disorders in a mammal, including a human, attention deficit disorders and pain (Armer R E and Miller D J, Exp. Opin. Ther. Patents, 11 (4): 563-572, 2001).

Thus, increasing activation of NMDA receptors via GlyT-1 inhibition may lead to agents that treat psychosis, schizophrenia, dementia and other diseases in which cognitive processes are impaired, such as attention deficit disorders or Alzheimer's disease.

SUMMARY OF THE INVENTION

The present invention provides compounds of formula I

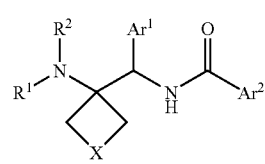

wherein
R¹ and R² are each independently lower alkyl, or together with the N-atom to which they are attached form a heterocyclic group selected from pyrrolidine, piperidine, piperazine, 4-methyl-piperazine, 4-cyclopropyl-piperazine, thiomorpholine, morpholine, 1-(3-oxa-8-aza-bicyclo[3.2.1]oct-8-yl and 1-(2-oxa-6-aza-spiro[3.3]hept-6-yl;
X is a bond, —CH$_2$— or —O—;
Ar¹ is aryl or heteroaryl, each of which is unsubstituted or substituted by one or two substituents selected from halogen, lower alkyl, lower alkoxy, and lower alkyl substituted by halogen;
Ar² is aryl or heteroaryl, each of which is unsubstituted or substituted by one, two or three substituents selected from halogen, lower alkyl, lower alkoxy, hydroxy, lower alkyl substituted by halogen, lower alkoxy substituted by halogen, S-lower alkyl, benzyl and phenyl;
or a pharmaceutically acceptable acid addition salt, racemic mixture, or enantiomer and/or optical isomer thereof.

Furthermore, the invention includes all racemic mixtures, all their corresponding enantiomers and/or optical isomers.

The present invention also provides pharmaceutical compositions containing compounds of formula I and manufacture of such compounds and compositions.

Compounds of general formula I are good inhibitors of the glycine transporter 1 (GlyT-1), and they have a good selectivity to glycine transporter 2 (GlyT-2) inhibitors. The invention provides methods for the treatment of neurological and neuropsychiatric disorders. In particular, compounds of the invention are useful for the treatment of diseases related to activation of NMDA receptors via Glyt-1 inhibition. Such diseases include, but are not limited to, the treatment of psychoses, dysfunction in memory and learning, schizophrenia, dementia and other diseases in which cognitive processes are impaired, such as attention deficit disorders or Alzheimer's disease.

The preferred indications using the compounds of the present invention are schizophrenia, cognitive impairment and Alzheimer's disease.

DETAILED DESCRIPTION OF THE INVENTION

The following definitions of general terms used herein apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a saturated straight- or branched-chain hydrocarbon group containing from 1 to 6 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes an alkyl group as described above, which is connected via an oxygen atom.

The term "halogen" denotes chlorine, iodine, fluorine and bromine.

The term "aryl" denotes a monovalent cyclic aromatic hydrocarbon radical consisting of one or two fused rings in which at least one ring is aromatic in nature, for example phenyl, benzyl, or naphthyl. The term aryl also denotes a group as defined above attached to additional rings, for example, biphenyl. The preferred aryl group is phenyl.

The term "heteroaryl" denotes a monovalent aromatic radical of one or two fused rings, which contains at least one heteroatom selected from N, O, and S, for example pyridyl, pyrazinyl, quinoxalinyl, 2,3-dihydro-benzo[1,4]dioxinyl, pyrimidinyl, pyridazinyl, pyrazolyl, benzo[b]thiophenyl, or 1,3,5-triazinyl.

The term "heterocyclic" denotes a non-aromatic radical containing one or two fused rings having at least one heteroatom selected from N, S, and O, for example oxetanyl, tetrahydrofuranyl, tetrahydropyranyl, azetidinyl, pyrrolidinyl, piperidinyl, piperazinyl, morpholinyl or thiomorpholinyl.

The term "alkyl, substituted by halogen" denotes a lower alkyl group as defined above in which one or more hydrogen atom has been replaced by a halogen atom, for example the following groups: $CF_3$, $CHF_2$, $CH_2F$, $CH_2CF_3$, $CH_2CHF_2$, $CH_2CH_2F$, $CH_2CH_2CF_3$, $CH_2CH_2CH_2CF_3$, $CH_2CH_2Cl$, $CH_2CF_2CF_3$, $CH_2CF_2CHF_2$, $CF_2CHFCF_3$, $C(CH_3)_2CF_3$, $CH(CH_3)CF_3$ or $CH(CH_2F)CH_2F$.

As used herein, the term "lower alkoxy substituted by halogen" denotes a lower alkoxy group as defined above wherein at least one hydrogen atom is replaced by halogen, for example the following groups: $OCF_3$, $OCHF_2$, $OCH_2F$, $OCH_2CF_3$, $OCH_2CHF_2$, $OCH_2CH_2F$, $OCH_2CH_2CF_3$, $OCH_2CH_2CH_2CF_3$, $OCH_2CH_2Cl$, $OCH_2CF_2CF_3$, $OCH_2CF_2CHF_2$, $OCF_2CHFCF_3$, $OC(CH_3)_2CF_3$, $OCH(CH_3)CF_3$ or $OCH(CH_2F)CH_2F$. The preferred group is $OCF_3$.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

Preferred compounds of the present application are compounds of formula I, wherein X is a bond, for example the following compounds:
2-methoxy-N-[phenyl-(1-pyrrolidin-1-yl-cyclopropyl)-methyl]-4,6-bis-trifluoromethyl-benzamide;
4-fluoro-2-methoxy-6-methylsulfanyl-N-[phenyl-(1-pyrrolidin-1-yl-cyclopropyl)-methyl]-benzamide;
2-methyl-N-[phenyl-(1-pyrrolidin-1-yl-cyclopropyl)-methyl]-4,6-bis-trifluoromethyl-benzamide;
2-methylsulfanyl-N-[phenyl-(1-pyrrolidin-1-yl-cyclopropyl)-methyl]-4,6-bis-trifluoromethyl-benzamide;
2-methoxy-6-methylsulfanyl-N-[phenyl-(1-pyrrolidin-1-yl-cyclopropyl)-methyl]-benzamide;
2-methoxy-6-methylsulfanyl-N-[phenyl-(1-pyrrolidin-1-yl-cyclopropyl)-methyl]-4-trifluoromethyl-benzamide;
(−)-2-methoxy-N-[phenyl-(1-pyrrolidin-1-yl-cyclopropyl)-methyl]-4,6-bis-trifluoromethyl-benzamide;
(−)-4-fluoro-2-methoxy-6-methylsulfanyl-N-[phenyl-(1-pyrrolidin-1-yl-cyclopropyl)-methyl]-benzamide;
(−)-2-methylsulfanyl-N-[phenyl-(1-pyrrolidin-1-yl-cyclopropyl)-methyl]-4,6-bis-trifluoromethyl-benzamide; and
2-methylsulfanyl-N-[phenyl-(1-pyrrolidin-1-yl-cyclopropyl)-methyl]-4-trifluoromethyl-benzamide.

Preferred compounds of the present application are further those, wherein X is —CH$_2$—, for example the following compounds
2-methylsulfanyl-N-[phenyl-(1-pyrrolidin-1-yl-cyclobutyl)-methyl]-4,6-bis-trifluoromethyl-benzamide;
4-fluoro-2-methoxy-6-methylsulfanyl-N-[phenyl-(1-pyrrolidin-1-yl-cyclobutyl)-methyl]-benzamide;

2-methoxy-6-methylsulfanyl-N-[phenyl-(1-pyrrolidin-1-yl-cyclobutyl)-methyl]-4-trifluoromethyl-benzamide;
2-methylsulfanyl-N-[phenyl-(1-pyrrolidin-1-yl-cyclobutyl)-methyl]-6-trifluoromethyl-benzamide;
2-methoxy-N-[phenyl-(1-pyrrolidin-1-yl-cyclobutyl)-methyl]-4,6-bis-trifluoromethyl-benzamide;
N-[phenyl-(1-pyrrolidin-1-yl-cyclobutyl)-methyl]-2,4-bis-trifluoromethyl-benzamide;
2-methylsulfanyl-N-[phenyl-(1-pyrrolidin-1-yl-cyclobutyl)-methyl]-4-trifluoromethyl-benzamide;
2-methoxy-N-[phenyl-(1-pyrrolidin-1-yl-cyclobutyl)-methyl]-4-trifluoromethyl-benzamide;
N-[(4-fluoro-phenyl)-(1-pyrrolidin-1-yl-cyclobutyl)-methyl]-2-methylsulfanyl-4-trifluoromethyl-benzamide;
(+)-2-methylsulfanyl-N-[phenyl-(1-pyrrolidin-1-yl-cyclobutyl)-methyl]-4,6-bis-trifluoromethyl-benzamide;
(−)-2-methylsulfanyl-N-[phenyl-(1-pyrrolidin-1yl-cyclobutyl)-methyl]-4,6-bis-trifluoromethyl-benzamide;
(+)-2-methoxy-6-methylsulfanyl-N-[phenyl-(1-pyrrolidin-1-yl-cyclobutyl)-methyl]-4-trifluoromethyl-benzamide;
(+)-2-methoxy-6-methylsulfanyl-N-[phenyl-(1-pyrrolidin-1-yl-cyclobutyl)-methyl]-4-trifluoromethyl-benzamide;
(+)-2-methylsulfanyl-N-[phenyl-(1-pyrrolidin-1-yl-cyclobutyl)-methyl]-4-trifluoromethyl-benzamide;
N-[(4-chloro-phenyl)-(1-pyrrolidin-1-yl-cyclobutyl)-methyl]-2-methylsulfanyl-4-trifluoromethyl-benzamide;
2-ethyl-N-[phenyl-(1-pyrrolidin-1-yl-cyclobutyl)-methyl]-4,6-bis-trifluoromethyl-benzamide;
N-[(4-fluoro-phenyl)-(1-pyrrolidin-1-yl-cyclobutyl)-methyl]-2-methoxy-6-methylsulfanyl-4-trifluoromethyl-benzamide;
N-[(4-chloro-phenyl)-1-pyrrolidin-1-yl-cyclobutyl)-methyl]-2-methoxy-6-methylsulfanyl-4-trifluoromethyl-benzamide;
N-[(3,5-difluoro-phenyl)-(1-pyrrolidin-1-yl-cyclobutyl)-methyl]-2-methylsulfanyl-4-trifluoromethyl-benzamide;
2-methyl-N-[phenyl-(1-pyrrolidin-1-yl-cyclobutyl)-methyl]-4-trifluoromethyl-benzamide;
2,4-Dichloro-N-[phenyl-(1-pyrrolidin-1-yl-cyclobutyl)-methyl]-benzamide;
N-[phenyl-(1-pyrrolidin-1-yl-cyclobutyl)-methyl]-2-trifluoromethyl-benzamide;
4-chloro-2-methoxy-N-[phenyl-(1-pyrrolidin-1-yl-cyclobutyl)-methyl]-benzamide;
2-methylsulfanyl-N-[phenyl-(1-piperidin-1-yl-cyclobutyl)-methyl]-4-trifluoromethyl-benzamide;
2-methoxy-6-methylsulfanyl-N-[phenyl-(1-piperidin-1-yl-cyclobutyl)-methyl]-4-trifluoromethyl-benzamide;
N-[(1-dimethylamino-cyclobutyl)-phenyl-methyl]-2-methylsulfanyl-4-trifluoromethyl-benzamide;
N-[(1-dimethylamino-cyclobutyl)-phenyl-methyl]-2-methoxy-6-methylsulfanyl-4-trifluoromethyl-benzamide;
2-bromo-N-[phenyl-(1-pyrrolidin-1-yl-cyclobutyl)-methyl]-4-trifluoromethyl-benzamide;
N-[(3,5-difluoro-phenyl)-(1-pyrrolidin-1-yl-cyclobutyl)-methyl]-2-methoxy-6-methylsulfanyl-4-trifluoromethyl-benzamide;
4-chloro-N-[phenyl-(1-pyrrolidin-1-yl-cyclobutyl)-methyl]-2-trifluoromethyl-benzamide;
N-[(3-fluoro-phenyl)-(1-pyrrolidin-1-yl-cyclobutyl)-methyl]-2-methylsulfanyl-4-trifluoromethyl-benzamide;
N-[(3-fluoro-phenyl)-(1-pyrrolidin-1-yl-cyclobutyl)-methyl]-2-methoxy-6-methylsulfanyl-4-trifluoromethyl-benzamide;
4-fluoro-2-methyl-N-[phenyl-(1-pyrrolidin-1-yl-cyclobutyl)-methyl]-benzamide;
2-methoxy-6-methylsulfanyl-N-[(1-morpholin-4-yl-cyclobutyl)-phenyl-methyl]-4-trifluoromethyl-benzamide;
4-chloro-2-methyl-N-[phenyl-(1-pyrrolidin-1-yl-cyclobutyl)-methyl]-benzamide;
2-methoxy-6-methylsulfanyl-N-[phenyl-(1-thiomorpholin-4-yl-cyclobutyl)-methyl]-4-trifluoromethyl-benzamide;
5-trifluoromethyl-biphenyl-2-carboxylic acid [phenyl-(1-pyrrolidin-1-yl-cyclobutyl)-methyl]-amide;
2-ethyl-N-[phenyl-(1-pyrrolidin-1-yl-cyclobutyl)-methyl]-4-trifluoromethyl-benzamide;
2-hydroxy-6-methylsulfanyl-N-[phenyl-(1-pyrrolidin-1-yl-cyclobutyl)-methyl]-4-trifluoromethyl-benzamide;
(rac)-2-methoxy-6-methylsulfanyl-N-{[1-(3-oxa-8-aza-bicyclo[3.2.1]oct-8-yl)-cyclobutyl]-phenyl-methyl}-4-trifluoromethyl-benzamide;
N-{[1-(4-cyclopropyl-piperazin-1-yl)-cyclobutyl]-phenyl-methyl}-2-methylsulfanyl-4-trifluoromethyl-benzamide;
N-{[1-(4-cyclopropyl-piperazin-1-yl)-cyclobutyl]-phenyl-methyl}-2-methoxy-6-methylsulfanyl-4-trifluoromethyl-benzamide;
2-methylsulfanyl-N-{[1-(2-oxa-6-aza-spiro[3.3]hept-6-yl)-cyclobutyl]-phenyl-methyl}-4-trifluoromethyl-benzamide; and
2-methoxy-6-methylsulfanyl-N-{[1-(2-oxa-6-aza-spiro[3.3]hept-6-yl)-cyclobutyl]-phenyl-methyl}-4-trifluoromethyl-benzamide.

Preferred compounds of the present application are further those, wherein X is —O—, for example the following compounds 2-methoxy-N-[phenyl-(3-pyrrolidin-1-yl-oxetan-3-yl)-1-methyl]-4,6-bis-trifluoromethyl-benzamide;
4-fluoro-2-methoxy-6-methylsulfanyl-N-[phenyl-(3-pyrrolidin-1-yl-oxetan-3-yl)-methyl]-benzamide;
2-methylsulfanyl-N-[phenyl-(3-pyrrolidin-1-yl-oxetan-3-yl)-methyl]-4,6-bis-trifluoromethyl-benzamide;
2-methoxy-6-methylsulfanyl-N-[phenyl-(3-pyrrolidin-1-yl-oxetan-3-yl)-methyl]-4-trifluoromethyl-benzamide;
2-methylsulfanyl-N-[phenyl-(3-pyrrolidin-1-yl-oxetan-3-yl)-methyl]-4-trifluoromethyl-benzamide;
(−)-2-methoxy-N-[phenyl-(3-pyrrolidin-1-yl-oxetan-3-yl)-methyl]-4,6-bis-trifluoromethyl-benzamide; and
(−)-4-fluoro-2-methoxy-6-methylsulfanyl-N-[phenyl-(3-pyrrolidin-1-yl-oxetan-3-yl)-methyl]-benzamide.

The present compounds of formula I and their pharmaceutically acceptable salts can be prepared by methods known in the art, for example, by processes (a)-(c) described below, which process comprises a) reacting a compound of formula

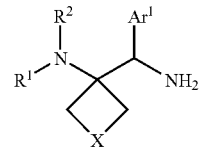

6 with a compound of formula

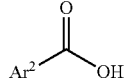

7 in the presence of HATU in dimethylformamide to obtain a compound of formula

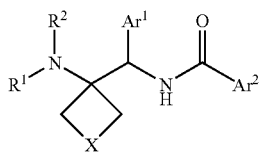

wherein the substituents $R^1$ and $R^2$, $Ar^1$, $Ar^2$ and X are as defined above, and if desired, converting the compounds obtained into pharmaceutically acceptable acid addition salts.

The compounds of formula I can be prepared in accordance with process variant a) and with the following schemes 1-2. The starting materials are either commercially available, are otherwise known in the chemical literature, or can be prepared in accordance with methods well known in the art.

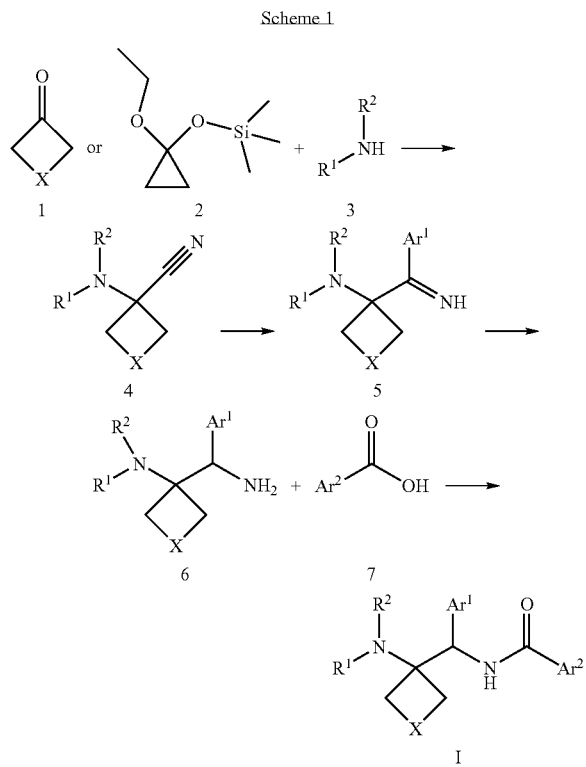

Compounds of formula I are synthesized according to scheme 1.

3-Oxetanone (1, X=O), cyclobutanone (1, X=CH$_2$) or ((1-ethoxycyclopropyl)oxy)trimethylsilane (2) are reacted with an amine $R^1R^2NH$ (3) and trimethylsilyl cyanide in acetic acid to yield intermediate 4. Cyanide 4 is reacted with an aryl lithium reagent, $Ar^1Li$, either commercially available or prepared in situ from an aryl iode $Ar^1I$ and tert. butyllithium. The intermediate imine 5 is used without purification and is reduced with sodium borohydride in methanol to the amine 6. Coupling of amine 6 with acid 7 is achieved with the coupling agent O-(7-azabenzotriazol-1-yl)-N,N,N',N'-tetramethyluronium hexafluorophosphate (=HATU) in dimethylformamide to obtain the final amides I.

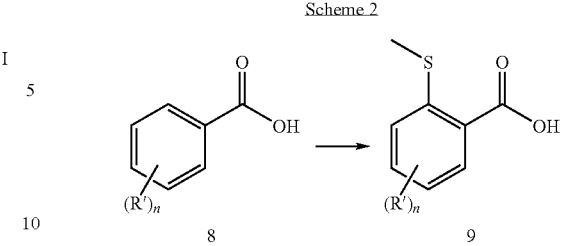

R' is halogen, lower alkyl, lower alkoxy, lower alkyl substituted by halogen, lower alkoxy substituted by halogen or phenyl; n is 0, 1 or 2.

Some acids are prepared according to scheme 2.

Acids 8 are deprotonated with sec-butyllithium/N,N,N'N'-tetramethylethylendiamine complex at −70° C. in THF. Quenching with dimethyl disulfide give ortho-methylsulfanyl benzoic acids 9.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I can be basic, for example in cases where the residue $R^3$ contains a basic group such as an aliphatic or aromatic amine moiety. In such cases the compounds of formula I can be converted to a corresponding acid addition salt.

The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or can be brought out of solution with a less polar solvent.

The acid addition salts of the basic compounds of formula I can be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention are good inhibitors of the glycine transporter I (GlyT-1). The compounds were investigated in accordance with the test given hereinafter.

Solutions and Materials

DMEM Complete Medium:
Nutrient mixture F-12 (Gibco Life-technologies), fetal bovine serum (FBS) 5%, (Gibco life technologies), Penicillin/Streptomycin 1% (Gibco life technologies), Hygromycin 0.6 mg/ml (Gibco life technologies), Glutamine 1 mM Gibco life technologies)

Uptake buffer (UB): 150 mM NaCl, 10 mM Hepes-Tris, pH 7.4, 1 M–M $CaCl_2$, 2.5 mM KCl, 2.5 mM $MgSO_4$, 10 mM (+) D-glucose.

Flp-in™-CHO (Invitrogen Cat n° R758-07) cells stably transfected with mGlyT1b cDNA.

Glycine Uptake Inhibition Assay (mGlyT-1b)

On day 1 mammalian cells, (Flp-in™-CHO), transfected with mGlyT-1b cDNA, were plated at the density of 40,000 cells/well in complete F-12 medium, without hygromycin in 96-well culture plates. On day 2, the medium was aspirated and the cells were washed twice with uptake buffer (UB). The cells were then incubated for 20 min at 22° C. with either (i) no potential competitor, (ii) 10 mM non-radioactive glycine, (iii) a concentration of a potential inhibitor. A range of concentrations of the potential inhibitor was used to generate data for calculating the concentration of inhibitor resulting in 50% of the effect (e.g. $IC_{50}$, the concentration of the competitor inhibiting glycine uptake of 50%). A solution was then immediately added containing [$^3$H]-glycine 60 nM (11-16 Ci/mmol) and 25 µM non-radioactive glycine. The plates were incubated with gentle shaking and the reaction was stopped by aspiration of the mixture and washing (three times) with ice-cold UB. The cells were lysed with scintillation liquid, shaken 3 hours and the radioactivity in the cells was counted using a scintillation counter.

The preferred compounds show an $IC_{50}$ (EM) at GlyT-1 in the range of 0.008-0.10. Data for some compounds are shown in the table below.

| Example No. | $IC_{50}$ (µM) uptake |
|---|---|
| 6 | 0.0683 |
| 9 | 0.0295 |
| 10 | 0.0253 |
| 11 | 0.0122 |
| 12 | 0.0112 |
| 13 | 0.034 |
| 14 | 0.0455 |
| 15 | 0.0312 |
| 16 | 0.0134 |
| 17 | 0.0368 |
| 24 | 0.0200 |
| 29 | 0.0509 |
| 30 | 0.047 |
| 31 | 0.0181 |
| 32 | 0.0225 |
| 33 | 0.00847 |
| 35 | 0.0098 |
| 36 | 0.0597 |
| 37 | 0.0398 |
| 38 | 0.0175 |
| 39 | 0.0211 |
| 40 | 0.0322 |
| 41 | 0.0148 |
| 43 | 0.0669 |
| 44 | 0.0951 |
| 47 | 0.0724 |
| 48 | 0.0275 |
| 49 | 0.0237 |
| 50 | 0.0100 |
| 51 | 0.0142 |
| 52 | 0.0127 |
| 53 | 0.0141 |
| 54 | 0.0275 |
| 55 | 0.0139 |
| 56 | 0.0135 |
| 57 | 0.0596 |
| 60 | 0.0496 |
| 63 | 0.0297 |
| 66 | 0.0915 |
| 67 | 0.0562 |
| 68 | 0.0091 |
| 69 | 0.0095 |
| 71 | 0.0521 |
| 72 | 0.0494 |
| 73 | 0.0308 |
| 74 | 0.0101 |
| 75 | 0.0261 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a process for the manufacture of pharmaceutical compositions. Such process comprises bringing the compound of formula I and/or pharmaceutically acceptable acid addition salt thereof and, for desired, one or more other therapeutically valuable substances into a galenical administration form together with one or more therapeutically inert carriers.

The most preferred indications in accordance with the present invention are those, which include disorders of the central nervous system, for example the treatment or prevention of schizophrenia, cognitive impairment and Alzheimer's disease.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

| Tablet Formulation (Wet Granulation) | | | | |
|---|---|---|---|---|
| Item | Ingredients | | mg/tablet | |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
|  | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Capsule Formulation | | | | |
|---|---|---|---|---|
| Item | Ingredients | | mg/capsule | |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
|  | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The following examples illustrate the invention but are not intended to limit its scope. The following abbreviations were used in the examples:
HATU: O-(7-azabenzotriazol-1-yl)-N,N,N',N'-tetramethyluronium hexafluorophosphate Synthesis of Intermediates Intermediate A 3-Pyrrolidin-1-yl-oxetane-3-carbonitrile

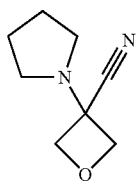

Pyrrolidine (7.4 g, 104 mmol) was slowly added at 0° C. to acetic acid (33 mL). 3-Oxetanone (1.5 g, 21 mmol) and trimethylsilyl cyanide (5.3 g, 52 mmol) were also added at 0° C. The reaction mixture was stirred at room temperature overnight and diluted with 100 mL dichloromethane. 32% sodium hydroxide solution was pH-9 (~50 mL). The mixture was extracted twice with dichloromethane. The combined organic phases were dried on sodium sulfate, filtered and carefully evaporated. Purification of the residue by flash chromatography on silica gel (dichloromethane/methanol 1:0→19:1) yielded 3-pyrrolidin-1-yl-oxetane-3-carbonitrile as a light yellow oil (3.22 g, contains 19% dichloromethane, 92%), MS: m/e=153.1 [(M+H)$^+$].

Intermediate B

C-Phenyl-C-(3-pyrrolidin-1-yl-oxetan-3-yl)-methylamine

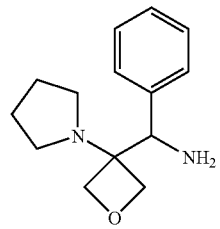

3-Pyrrolidin-1-yl-oxetane-3-carbonitrile (intermediate A, 1.6 g, 91% purity, 10 mmol) was dissolved in 10 mL tetrahydrofurane. Phenyllithium (2M in dibutylether, 9.8 mL, 20 mmol) was added dropwise at −5° C. The reaction mixture was stirred at room temperature for 1.5 hours and poured into cold saturated sodium bicarbonate solution. The mixture was extracted three times with ethyl acetate. The combined organic phases were dried on sodium sulfate, filtered and evaporated. The residue was dissolved in 35 mL methanol and sodiumborohydride (0.77 g, 20 mmol) was added portionwise at 0° C. The reaction mixture was stirred at room temperature for 2 hours and quenched by addition of water. The solvent was evaporated off. The residue was taken up in water and ethyl acetate and was extracted three times with ethyl acetate. The combined organic phases were dried on sodium sulfate, filtered and evaporated. The crude product (brown oil, 2.26 g, 99%) was used for the next step without further purification, MS: m/e=216.3 [(M−NH$_2$)$^+$].

Intermediate C

1-Pyrrolidin-1-yl-cyclopropanecarbonitrile

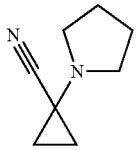

The title compound, colorless liquid, was prepared in accordance with the general method of intermediate A from ((1-ethoxycyclopropyl)oxy)trimethylsilane and pyrrolidine.

Intermediate D

C-Phenyl-C-(1-pyrrolidin-1-yl-cyclopropyl)-methylamine

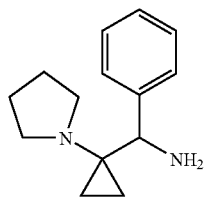

The title compound, light yellow liquid, MS: m/e=200.3 [(M−NH$_2$)$^+$], was prepared in accordance with the general method of intermediate B from 1-pyrrolidin-1-yl-cyclopropanecarbonitrile (intermediate C) and phenyllithium.

Intermediate E

2-Methoxy-6-methylsulfanyl-benzoic acid

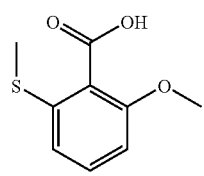

N,N,N'N'-Tetramethylethylendiamine (16 g, 138 mmol) was added drop-wise at −70° C. to a solution of sec-butyllithium (92 mL, 1.3 M in cyclohexane, 120 mmol) in 80 mL tetrahydrofuran. 2-Methoxybenzoic acid (7.0 g, 46 mmol) in 40 mL tetrahydrofuran was added drop-wise at −70° C. over 2 hours. After complete addition stirring was continued at −70° C. for another 2 hours. Dimethyl disulfide (15.2 g, 161 mmol) was added at −70° C. within 10 min. Stirring was continued at −70° C. for another hour and the reaction was allowed to slowly warm up over night. The reaction mixture was quenched with 40 mL water and extracted with 200 mL ethyl acetate. The aqueous phase was adjusted to pH1 by addition of 25% HCl and extracted twice with dichloromethane. The combined organic phases were dried on sodium sulfate, filtered and evaporated. The crude product was crystallized with cyclohexane and yielded the title compound as an off-white solid (2.7 g, 30%), MS: m/e=197.4 [(M−H)$^-$].

Intermediate F

1-Pyrrolidin-1-yl-cyclobutanecarbonitrile

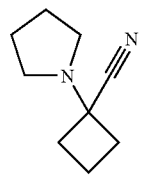

The title compound, colorless liquid, MS: m/e=151.1 [(M+H)$^+$], was prepared in accordance with the general method of intermediate A from cyclobutanone and pyrrolidine.

Intermediate G

C-Phenyl-C-(1-pyrrolidin-1-yl-cyclobutyl)-methylamine

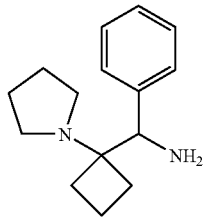

The title compound, light yellow liquid, MS: m/e=231.1 [(M+H)$^+$], was prepared in accordance with the general method of intermediate B from 1-pyrrolidin-1-yl-cyclobutanecarbonitrile (intermediate F) and phenyllithium.

Intermediate H

2-Methoxy-6-methylsulfanyl-4-trifluoromethyl-benzoic acid

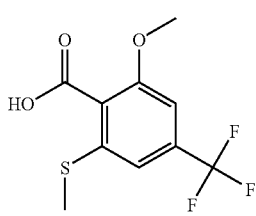

The title compound, white solid, MS: m/e=265.1 [(M−H)⁻], was prepared in accordance with the general method of intermediate E from 2-methoxy-4-(trifluoromethyl)benzoic acid and dimethyl disulfide.

Intermediate I

2-Methylsulfanyl-6-trifluoromethyl-benzoic acid

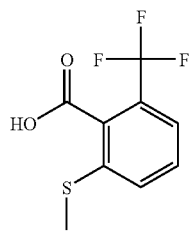

The title compound, white solid, MS: m/e=191.1 [(M−CO₂H)⁻], was prepared in accordance with the general method of intermediate E from 2-(trifluoromethyl)benzoic acid and dimethyl disulfide.

Intermediate J

2-Methylsulfanyl-4-trifluoromethyl-benzoic acid

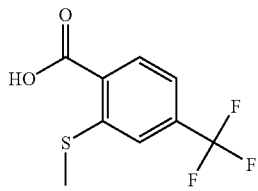

The title compound, white solid, MS: m/e=235.0 [(M−H)⁻], was prepared in accordance with the general method of intermediate E from 4-(trifluoromethyl)benzoic acid and dimethyl disulfide.

Intermediate K

C-(4-Fluorophenyl)-C-(1-pyrrolidin-1-yl-cyclobutyl)-methylamine

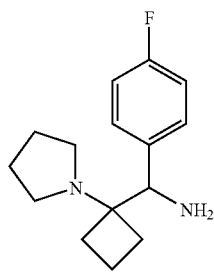

tert-Butyllithium (1.6M in pentane, 65 mL, 104 mmol) was added during 30 min at −75° C. to −60° C. to a solution of 4-fluoroiodobenzene (13 g, 59 mmol) in 40 mL diethylether.

The reaction mixture was stirred at −75° C. for 45 min. 1-Pyrrolidin-1-yl-cyclobutanecarbonitrile (intermediate F) (5 g, 29 mmol) in 5 mL diethylether was added slowly. The reaction mixture was allowed to slowly warm up and was poured into cold saturated sodium bicarbonate solution. The mixture was extracted three times with ethyl acetate. The combined organic phases were dried on sodium sulfate, filtered and evaporated. The residue was dissolved in 100 mL methanol and sodiumborohydride (2.3 g, 59 mmol) was added portion-wise at 0° C. The reaction mixture was stirred at room temperature for 2 hours and quenched by addition of water. The solvent was evaporated off. The residue was taken up in water and ethyl acetate and was extracted three times with ethyl acetate. The combined organic phases were dried on sodium sulfate, filtered and evaporated. Purification of the residue by flash chromatography on amine silica gel with dichloromethane yielded the title compound as a yellow oil (6.25 g, 85%), MS: m/e=249.2 [(M+H)⁺].

Intermediate L

C-(4-Chloro-phenyl)-C-(1-pyrrolidin-1-yl-cyclobutyl)-methylamine

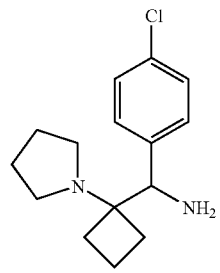

The title compound, yellow oil, MS: m/e=265.2 [(M+H)⁺], was prepared in accordance with the general method of intermediate K from 1-pyrrolidin-1-yl-cyclobutanecarbonitrile (intermediate F) and 1-chloro-4-iodobenzene.

Intermediate M

2-Ethyl-4,6-bis-trifluoromethyl-benzoic acid

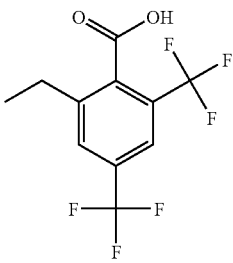

The title compound, white solid, MS: m/e=285.2 [(M−H)⁻], was prepared in accordance with the general method of intermediate E from 2,4-bis(trifluoromethyl)benzoic acid and iodomethane.

Intermediate N

C-(3,5-Difluoro-phenyl)-C-(1-pyrrolidin-1-yl-cyclobutyl)-methylamine

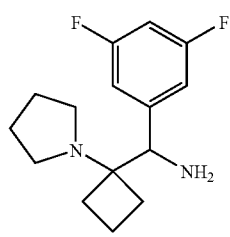

The title compound, yellow oil, MS: m/e=267.2 [(M+H)⁺], was prepared in accordance with the general method of intermediate K from 1-pyrrolidin-1-yl-cyclobutanecarbonitrile (intermediate F) and 3,5-difluoro-iodobenzene.

Intermediate O

1-Piperidin-1-yl-cyclobutanecarbonitrile

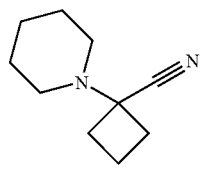

The title compound, light yellow liquid, MS: m/e=165.2 [(M+H)⁺], was prepared in accordance with the general method of intermediate A from cyclobutanone and piperidine.

Intermediate P

C-Phenyl-C-(1-piperidin-1-yl-cyclobutyl)-methylamine

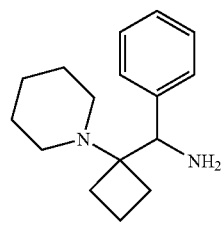

The title compound, light yellow liquid, MS: m/e=245.3 [(M+H)⁺], was prepared in accordance with the general method of intermediate B from 1-piperidin-1-yl-cyclobutanecarbonitrile (intermediate O) and phenyllithium.

Intermediate Q

1-Dimethylamino-cyclobutanecarbonitrile

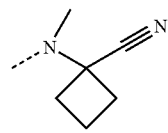

The title compound, colorless liquid, MS: m/e=125.1 [(M+H)⁺], was prepared in accordance with the general method of intermediate A from cyclobutanone and dimethylamine hydrochloride.

Intermediate R

[1-(Amino-phenyl-methyl)-cyclobutyl]-dimethylamine

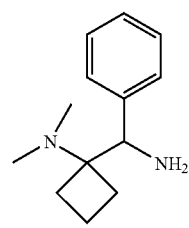

The title compound, yellow liquid, MS: m/e=205.2 [(M+H)⁺], was prepared in accordance with the general method of intermediate B from 1-dimethylamino-cyclobutanecarbonitrile (intermediate Q) and phenyllithium.

Intermediate S

C-(3-Fluoro-phenyl)-C-(1-pyrrolidin-1-yl-cyclobutyl)-methylamine

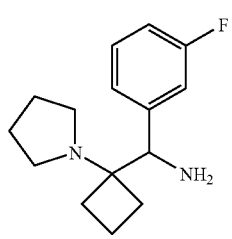

The title compound, yellow, oil, MS: m/e=249.2 [(M+H)⁺], was prepared in accordance with the general method of intermediate K from 1-pyrrolidin-1-yl-cyclobutanecarbonitrile (intermediate F) and 3-fluoro-iodobenzene.

Intermediate T

1-Morpholin-4-yl-cyclobutanecarbonitrile

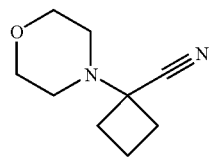

The title compound, light yellow liquid, was prepared in accordance with the general method of intermediate A from cyclobutanone and morpholine.

Intermediate U

C-(1-Morpholin-4-yl-cyclobutyl)-C-phenyl-methylamine

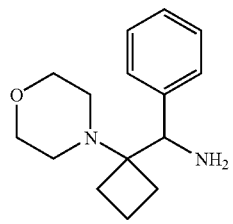

The title compound, light yellow liquid, MS: m/e=247.3 [(M+H)⁺], was prepared in accordance with the general method of intermediate B from 1-morpholin-4-yl-cyclobutanecarbonitrile (intermediate T) and phenyllithium.

Intermediate V 1-(4-Methyl-piperazin-1-yl)-cyclobutanecarbonitrile

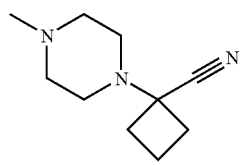

The title compound, light yellow liquid, MS: m/e=180.2 [(M+H)⁺], was prepared in accordance with the general method of intermediate A from cyclobutanone and 1-methylpiperazine.

Intermediate W

C-[1-(4-Methyl-piperazin-1-yl)-cyclobutyl]-C-phenyl-methylamine

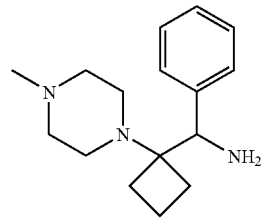

The title compound, yellow liquid, MS: m/e=260.2 [(M+H)⁺], was prepared in accordance with the general method of intermediate B from 1-(4-methyl-piperazin-1-yl)-cyclobutanecarbonitrile (intermediate V) and phenyllithium.

Intermediate X

1-Thiomorpholin-4-yl-cyclobutanecarbonitrile

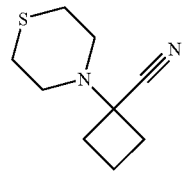

The title compound, white solid, MS: m/e=182.9 [(M+H)⁺], was prepared in accordance with the general method of intermediate A from cyclobutanone and thiomorpholine.

Intermediate Y

C-Phenyl-C-(1-thiomorpholin-4-yl-cyclobutyl)-methylamine

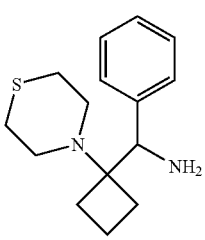

The title compound, yellow oil, MS: m/e=263.1 [(M+B)⁺], was prepared in accordance with the general method of intermediate B from 1-thiomorpholin-4-yl-cyclobutanecarbonitrile (intermediate X) and phenyllithium.

Intermediate Z

5-Trifluoromethyl-biphenyl-2-carboxylic acid

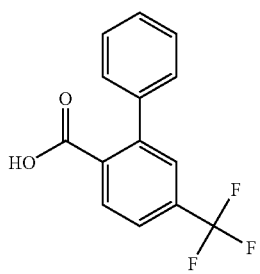

2-Bromo-4-trifluoromethyl-benzoic acid (100 mg, 0.372 mmol) and phenylboronic acid (70 mg, 0.574 mmol) were dissolved in 6 mL dioxane and 3 mL 1N sodium carbonate solution. The mixture was evacuated and back-filled with argon several times to remove oxygen. 2-Dicyclohexylphosphino-2',6'-dimethoxy-1,1'-biphenyl (S-Phos, 31 mg, 0.075 mmol) and palladium acetate (8 mg, 0.036 mmol) were added and the reaction mixture was refluxed overnight. The mixture was diluted with ethyl acetate, water and 2N sodium carbonate solution. The mixture was extracted three times with 2N sodium carbonate solution and the aqueous layers washed with ethyl acetate. The combined organic layers were discarded. The combined aqueous layers were acidified with 2N HCl and extracted twice with dichloromethane. The organic layers were washed with brine, combined, dried over sodium sulfate, filtered and concentrated down. Purification of the residue by flash chromatography on gel with dichloromethane/methanol/acetic acid (100:0:0→90:10:0.5) yielded the title compound as a white solid (63 mg, 64%).

Intermediate AA

2-Hydroxy6-methylsulfanyl-4-trifluoromethyl-benzoic acid

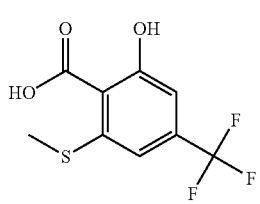

The title compound, white solid, was obtained as a by-product in the synthesis of 2-methoxy-6-methylsulfanyl-4-trifluoromethyl-benzoic acid (intermediate H).

Intermediate AB 1-(3-Oxa-8-aza-bicyclo[3.2.1]oct-8-yl)-cyclobutanecarbonitrile

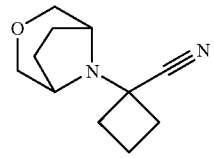

The title compound was prepared in accordance with the general method of intermediate A from cyclobutanone and 3-oxa-8-aza-bicyclo[3.2.1]octane hydrochloride (CAS 904316-92-3).

Intermediate AC

C-[1-3-Oxa-8-aza-bicyclo[3.2.1]oct-8-yl)-cyclobutyl]-C-phenyl-methylamine

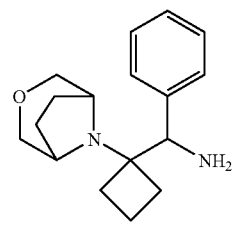

The title compound was prepared in accordance with the general method of intermediate B from 1-(3-oxa-8-aza-bicyclo[3.2.1]oct-8-yl)-cyclobutanecarbonitrile (intermediate AB) and phenyllithium.

Intermediate AD 1-(4-Cyclopropyl-piperazin-1-yl)-cyclobutanecarbonitrile

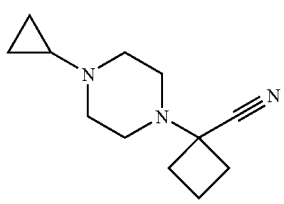

The title compound, colourless oil, MS: m/e=179.1 [(M−CN)+], was prepared in accordance with the general method of intermediate A from cyclobutanone and 1-cyclopropyl-piperazine.

Intermediate AE

C-[1-(4-Cyclopropyl-piperazin-1-yl)-cyclobutyl]-C-phenyl-methylamine

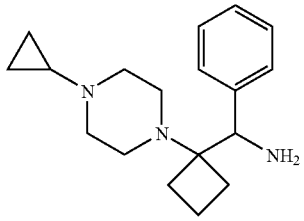

The title compound, yellow liquid, MS: m/e=286.2 [(M+H)+], was prepared in accordance with the general method or intermediate B from 1-(4-cyclopropyl-piperazin-1-yl)-cyclobutanecarbonitrile (intermediate V) and phenyllithium.

Intermediate AF 1-(2-Oxa-6-aza-spiro[3.3]hept-6-yl)-cyclobutanecarbonitrile

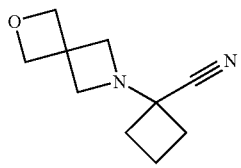

The title compound was prepared in accordance with the general method of intermediate A from cyclobutanone and 2-oxa-6-aza-spiro[3.3]heptane oxalate (CAS 1045709-32-7).

Intermediate AG

C-[1-(2-Oxa-6-aza-spiro[3.3]hept-6-yl)-cyclobutyl]-C-phenyl-methylamine

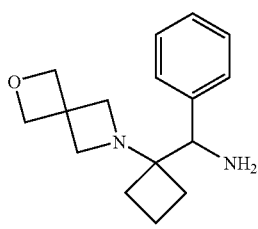

The title compound, yellow oil, MS: m/e=259.1 [(M+H)+], was prepared in accordance with the general method of intermediate B from 1-(2-oxa-6-aza-spiro[3.3]hept-6-yl)-cyclobutanecarbonitrile (intermediate AF) and phenyllithium.

SYNTHESIS OF THE EXAMPLES

Example 1

2-Methoxy-N-[phenyl-(3-pyrrolidin-1-yl-oxetan-3-yl)-methyl]-4,6-bis-trifluoromethyl-benzamide

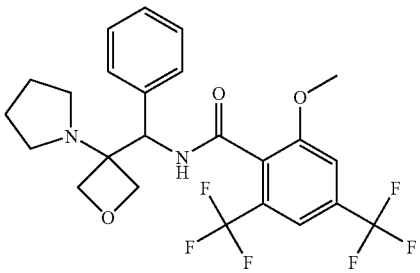

2,4-Bis(trifluoromethyl)-6-methoxybenzoic acid (155 mg, 0.538 mmol) was dissolved in 2 mL dimethylformamide. N,N-Diisopropylethylamine (78 mg, 0.605 mmol) and O-(7-azabenzotriazol-1-yl)-N,N,N',N'-tetramethyluronium hexafluorophosphate (205 mg, 0.539 mmol) were added. After 5 minutes of stirring at room temperature C-phenyl-C-(3-pyrrolidin-1-yl-oxetan-3-yl)-methylamine (intermediate B) (125 mg, 0.539 mmol) in 2 mL dimethylformamide was added. The reaction mixture was stirred at room temperature overnight. The solvent was evaporated off. The residue was taken up in 2N sodium carbonate solution and ethyl acetate and was extracted three times with ethyl acetate. The combined organic phases were dried on sodium sulfate, filtered and evaporated. Purification of the residue by flash chromatography on silica gel (heptane/ethyl acetate 1:0-1:1) yielded 2-methoxy-N-[phenyl-(3-pyrrolidin-1-yl-oxetan-3-yl)-methyl]-4,6-bis-trifluoromethyl-benzamide as an off-white solid (173 mg, 64%), MS: m/e=503.2 [(M+H)+].

The following examples were prepared according to the method in examples 1:

| | Structure | Name | MS: m/e | Acid | Amine |
|---|---|---|---|---|---|
| 2 | 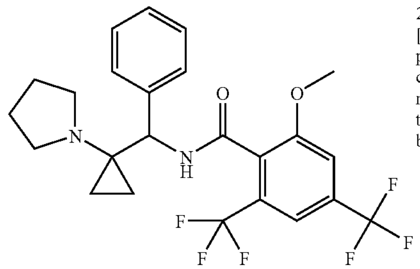 | 2-Methoxy-N-[phenyl-(1-pyrrolidin-1-yl-cyclopropyl)-methyl]-4,6-bis-trifluoromethyl-benzamide | 487.3 [(M + H)+] | 2,4-Bis(trifluoromethyl)-6-methoxybenzoic acid | C-Phenyl-C-(1-pyrrolidin-1-yl-cyclopropyl)-methylamine (intermediate D) |
| 3 | 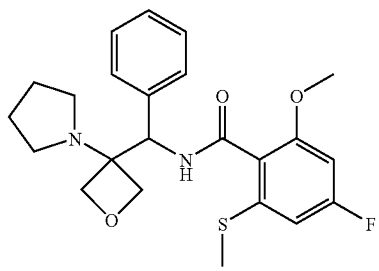 | 4-Fluoro-2-Methoxy-6-methylsulfanyl-N-[phenyl-(3-pyrrolidin-1-yl-oxetan-3-yl)-methyl]-benzamide | 431.3 [(M + H)+] | 4-Fluoro-2-methoxy-6-methylsulfanyl-benzoic acid (CAS 960531-01-5) | C-phenyl-C-(3-pyrrolidin-1-yl-oxetan-3-yl)-methylamine (intermediate B) |
| 4 | 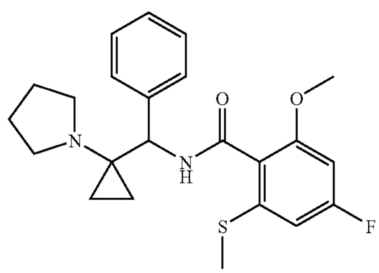 | 4-Fluoro-2-Methoxy-6-methylsulfanyl-N-[phenyl-(1-pyrrolidin-1-yl-cyclopropyl)-methyl]-benzamide | 415.3 [(M + H)+] | 4-Fluoro-2-methoxy-6-methylsulfanyl-benzoic acid (CAS 960531-01-5) | C-phenyl-C-(1-pyrrolidin-1-yl-cyclopropyl)-methylamine (intermediate D) |
| 5 | 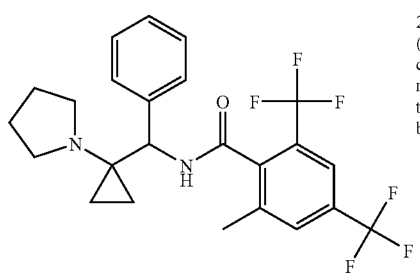 | 2-Methyl-N-[phenyl-(1-pyrrolidin-1-yl-cyclopropyl)-methyl]-4,6-bis-trifluoromethyl-benzamide | 471.2 [(M + H)+] | 2-Methyl-4,6-bis-trifluoromethyl-benzoic acid (CAS 895580-37-7) | C-Phenyl-C-(1-pyrrolidin-1-yl-cyclopropyl)-methylamine (intermediate D) |
| 6 | 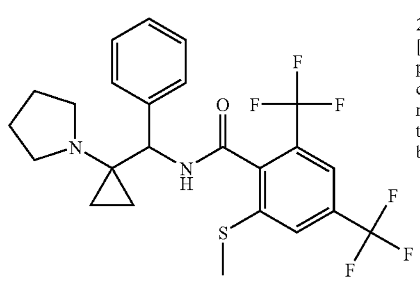 | 2-Methylsulfanyl-N-[phenyl-(1-pyrrolidin-1-yl-cyclopropyl)-methyl]-4,6-bis-trifluoromethyl-benzamide | 503.2 [(M + H)+] | 2-Methylsulfanyl-4,6-bis-trifluoromethyl-benzoic acid (CAS 896120-49-3) | C-Phenyl-C-(1-pyrrolidin-1-yl-cyclopropyl)-methylamine (intermediate D) |

-continued

| | Structure | Name | MS: m/e | Acid | Amine |
|---|---|---|---|---|---|
| 7 | 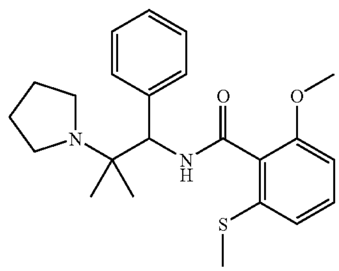 | 2-Methoxy-6-methylsulfanyl-N-[phenyl-(1-pyrrolidin-1-yl-cyclopropyl)-methyl]-benzamide | 397.3 [(M + H)⁺] | 2-Methoxy-6-methylsulfanyl-benzoic acid (intermediate E) | C-phenyl-C-(1-pyrrolidin-1-yl-cyclopropyl)-methylamine (intermediate D) |
| 8 | 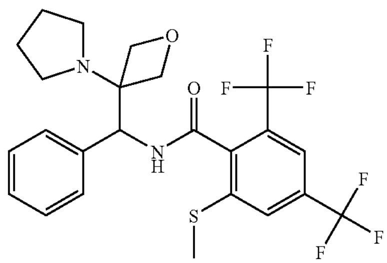 | 2-Methylsulfanyl-N-[phenyl-(3-pyrrolidin-1-yl-oxetan-3-yl)-methyl]-4,6-bis-trifluoromethyl-benzamide | 519.2 [(M + H)⁺] | 2-Methylsulfanyl-4,6-bis-trifluoromethyl-benzoic acid (CAS 896120-49-3) | C-Phenyl-C-(3-pyrrolidin-1-yl-oxetan-3-yl)-methylamine (intermediate B) |
| 9 | 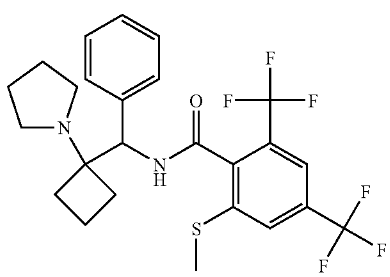 | 2-Methylsulfanyl-N-[phenyl-(1-pyrrolidin-1-yl-cyclobutyl)-methyl]-4,6-bis-trifluoromethyl-benzamide | 517.2 [(M + H)⁺] | 2-Methylsulfanyl-4,6-bis-trifluoromethyl-benzoic acid (CAS 896120-49-3) | C-Phenyl-C-(1-pyrrolidin-1-yl-cyclobutyl)-methylamine (intermediate G) |
| 10 | 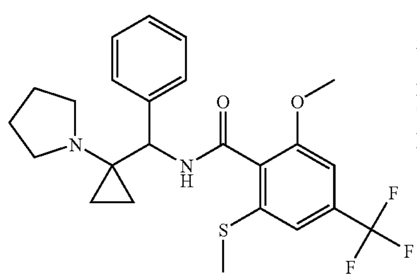 | 2-Methoxy-6-methylsulfanyl-N-[phenyl-(1-pyrrolidin-1-yl-cyclopropyl)-methyl]-4-trifluoromethyl-benzamide | 465.3 [(M + H)⁺] | 2-Methylsulfanyl-4,6-bis-trifluoromethyl-benzoic acid (CAS 896120-49-3) | C-Phenyl-C-(1-pyrrolidin-1-yl-cyclopropyl)-methylamine (intermediate D) |
| 11 | 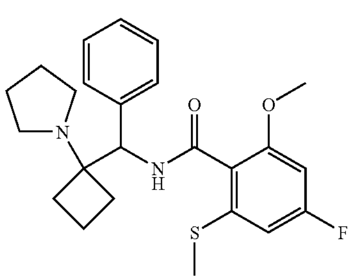 | 4-Fluoro-2-Methoxy-6-methylsulfanyl-N-[phenyl-(1-pyrrolidin-1-yl-cyclobutyl)-methyl]-benzamide | 429.3 [(M + H)⁺] | 4-Fluoro-2-methoxy-6-methylsulfanyl-benzoic acid (CAS 960531-01-5) | C-phenyl-C-(1-pyrrolidin-1-yl-cyclobutyl)-methylamine (intermediate G) |

-continued

| | Structure | Name | MS: m/e | Acid | Amine |
|---|---|---|---|---|---|
| 12 | 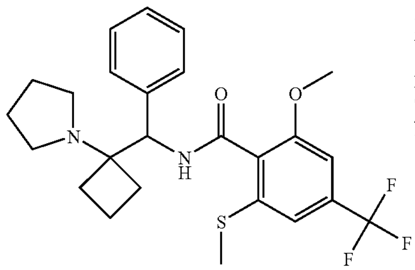 | 2-Methoxy-6-methylsulfanyl-N-[phenyl-(1-pyrrolidin-1-yl-cyclobutyl)-methyl]-4-trifluoromethyl-benzamide | 479.2 [(M + H)⁺] | 2-Methoxy-6-methylsulfanyl-4-trifluoromethyl-benzoic acid (intermediate H) | C-phenyl-C-(1-pyrrolidin-1-yl-cyclobutyl)-methylamine (intermediate G) |
| 13 | 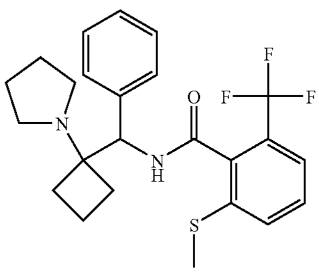 | 2-Methylsulfanyl-N-[phenyl-(1-pyrrolidin-1-yl-cyclobutyl)-methyl]-6-trifluoromethyl-benzamide | 449.2 [(M + H)⁺] | 2-Methylsulfanyl-6-trifluoromethyl-benzoic acid (intermediate I) | C-Phenyl-C-(1-pyrrolidin-1-yl-cyclobutyl)-methylamine (intermediate G) |
| 14 | 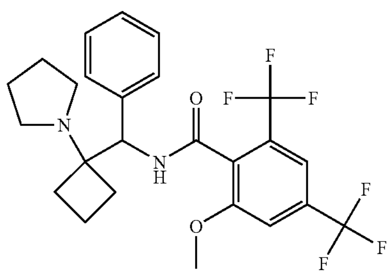 | 2-Methoxy-N-[phenyl-(1-pyrrolidin-1-yl-cyclobutyl)-methyl]-4,6-bis-trifluoromethyl-benzamide | 501.3 [(M + H)⁺] | 2,4-Bis(trifluoromethyl)-6-methoxybenzoic acid | C-Phenyl-C-(1-pyrrolidin-1-yl-cyclobutyl)-methylamine (intermediate G) |
| 15 | 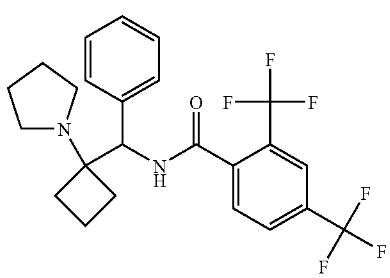 | N-[Phenyl-(1-pyrrolidin-1-yl-cyclobutyl)-methyl]-2,4-bis-trifluoromethyl-benzamide | 471.2 [(M + H)⁺] | 2,4-Bis trifluoromethyl) benzoic acid | C-Phenyl-C-(1-pyrrolidin-1-yl-cyclobutyl)-methylamine (intermediate G) |
| 16 | 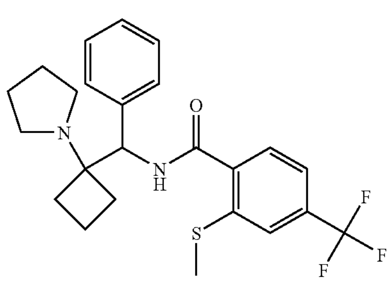 | 2-Methylsulfanyl-N-[phenyl-(1-pyrrolidin-1-yl-cyclobutyl)-methyl]-4-trifluoromethyl-benzamide | 449.3 [(M + H)⁺] | 2-Methylsulfanyl-4-trifluoromethyl-benzoic acid (intermediate J) | C-Phenyl-C-(1-pyrrolidin-1-yl-cyclobutyl)-methylamine (intermediate G) |

-continued

| | Structure | Name | MS: m/e | Acid | Amine |
|---|---|---|---|---|---|
| 17 | 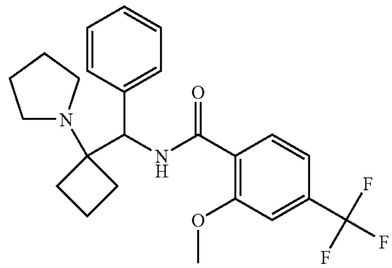 | 2-Methoxy-N-[phenyl-(1-pyrrolidin-1-yl-cyclobutyl)-methyl]-4-trifluoromethyl-benzamide | 433.3 [(M + H)⁺] | 2-Methoxy-4-(trifluoromethyl) benzoic acid | C-Phenyl-C-(1-pyrrolidin-1-yl-cyclobutyl)-methylamine (intermediate G) |
| 18 | 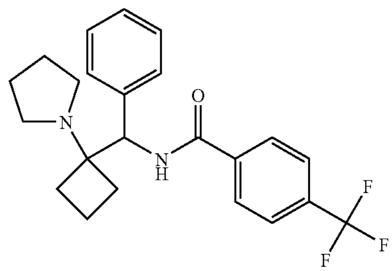 | N-[Phenyl-(1-pyrrolidin-1-yl-cyclobutyl)-methyl]-4-trifluoromethyl-benzamide | 403.5 [(M + H)⁺] | 4-(Trifluoromethyl) benzoic acid | C-Phenyl-C-(1-pyrrolidin-1-yl-cyclobutyl)-methylamine (intermediate G) |
| 19 | 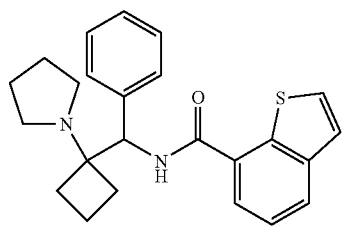 | Benzo[b]thiophene-7-carboxylic acid [phenyl-(1-pyrrolidin-1-yl-cyclobutyl)-methyl]-amide | 391.1 [(M + H)⁺] | Benzo[b]thiophene-7-carboxylic acid | C-Phenyl-C-(1-pyrrolidin-1-yl-cyclobutyl)-methylamine (intermediate G) |
| 20 | 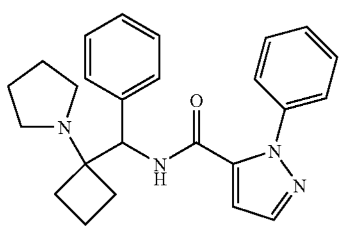 | 2-Phenyl-2H-pyrazole-3-carboxylic acid [phenyl-(1-pyrrolidin-1-yl-cyclobutyl)-methyl]-amide | 401.4 [(M + H)⁺] | 1-Phenyl-1H-pyrazole-5-carboxylic acid | C-Phenyl-C-(1-pyrrolidin-1-yl-cyclobutyl)-methylamine (intermediate G) |
| 21 | 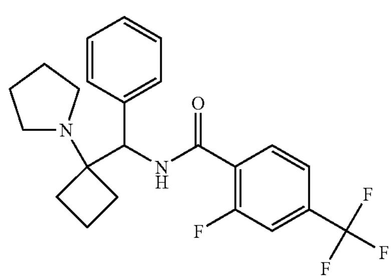 | 2-Fluoro-N-[phenyl-(1-pyrrolidin-1-yl-cyclobutyl)-methyl]-4-trifluoromethyl-benzamide | 421.2 [(M + H)⁺] | 2-Fluoro-4-(trifluoromethyl) benzoic acid | C-Phenyl-C-(1-pyrrolidin-1-yl-cyclobutyl)-methylamine (intermediate G) |
| 22 | 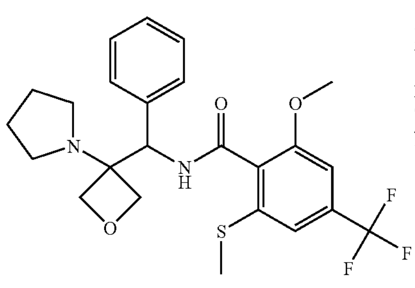 | 2-Methoxy-6-methylsulfanyl-N-[phenyl-(3-pyrrolidin-1-yl-oxetan-3-yl)-methyl]-4-trifluoromethyl-benzamide | 481.2 [(M + H)⁺] | 2-Methoxy-6-methylsulfanyl-4-trifluoromethyl-benzoic acid (intermediate H) | C-phenyl-C-(3-pyrrolidin-1-yl-oxetan-3-yl)-methylamine (intermediate B) |

-continued

| | Structure | Name | MS: m/e | Acid | Amine |
|---|---|---|---|---|---|
| 23 | 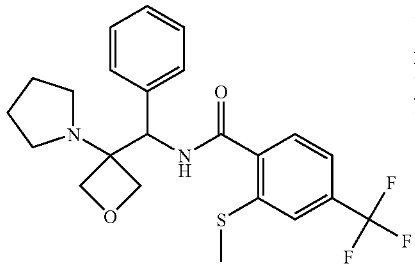 | 2-Methylsulfanyl-N-[phenyl-(3-pyrrolidin-1-yl-oxetan-3-yl)-methyl]-4-trifluoromethyl-benzamide | 451.1 [(M + H)+] | 2-Methylsulfanyl-4-trifluoromethyl-benzoic acid (intermediate J) | C-Phenyl-C-(3-pyrrolidin-1-yl-oxetan-3-yl) methylamine (intermediate B) |
| 24 | 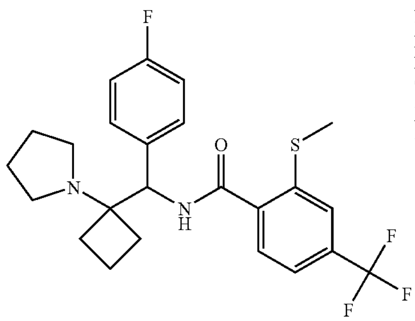 | N-[(4-Fluoro-phenyl)-(1-pyrrolidin-1-yl-cyclobutyl)-methyl]-2-methylsulfanyl-4-trifluoromethyl-benzamide | 467.2 [(M + H)+] | 2-Methylsulfanyl-4-trifluoromethyl-benzoic acid (intermediate J) | C-(4-Fluoro-phenyl)-C-(1-pyrrolidin-1-yl-cylcobutyl)-methylamine (intermediate K) |

The following examples were prepared by separation on chiral HPLC of the corresponding recemic mixture.

| No | Name | Racemate example No | Chiral Column | Solvent | Retention time |
|---|---|---|---|---|---|
| 25 | (−)-2-Methoxy-N-[phenyl-(1-pyrrolidin-1-yl-cyclopropyl)-methyl]-4,6-bis-trifluoromethyl-benzamide | 2 | Chiralpak AD | 5% ethanol in heptane | 85 min |
| 26 | (−)-2-Methoxy-N-[phenyl-(3-pyrrolidin-1-yl-oxetan-3-yl)-methyl]-4,6-bis-trifluoromethyl-benzamide | 1 | Chiralpak AD | 7% ethanol in heptane | 71 min |
| 27 | (−)-4-Fluoro-2-methoxy-6-methylsulfanyl-N-[phenyl-(3-pyrrolidin-1-yl-oxctan-3-yl)-methyl]-benzamide | 3 | Chiralpak AD | 15% isopropanol in heptane | 107 min |
| 28 | (−)-4-Fluoro-2-methoxy-6-methylsulfanyl-N-[phenyl-(1-pyrrolidin-1-yl-cyclopropyl)-methyl]-benzamide | 4 | Chiralpak AD | 15% isopropanol in heptane | 99 min |
| 29 | (−)-2-Methylsulfanyl-N-[phenyl-(1-pyrrolidin-1-yl-cyclopropyl)-methyl]-4,6-bis-trifluoromethyl-benzamide | 6 | Chiralpak AD | 5% isopropanol in heptane | 61 min |
| 30 | (+)-2-Methylsulfanyl-N-[phenyl-(1-pyrrolidin-1-yl-cyclobutyl)-methyl]-4,6-bis-trifluoromethyl-benzamide | 9 | Chiralpak AD | 5% isopropanol in heptane | 46 min |
| 31 | (−)-2-Methylsulfanyl-N-[phenyl-(1-pyrrolidin-1-yl-cyclobutyl)-methyl]-4,6-bis-trifluoromethyl-benzamide | 9 | Chiralpak AD | 5% isopropanol in heptane | 73 min |
| 32 | (+)-2-Methoxy-6-methylsulfanyl-N-[phenyl-(1-pyrrolidin-1-yl-cyclobutyl)-methyl]-4-trifluoromethyl-benzamide | 12 | Chiralpak AD | 30% isopropanol in heptane | 46 min |
| 33 | (+)-2-Methoxy-6-methylsulfanyl-N-[phenyl-(1-pyrrolidin-1-yl-cyclobutyl)-methyl]-4-trifluoromethyl-benzamide | 12 | Chiralpak AD | 30% isopropanol in heptane | 89 min |
| 34 | (−)-2-Methylsulfanyl-N-[phenyl-(1-pyrrolidin-1-yl-cyclobutyl)-methyl]-4-trifluoromethyl-benzamide | 6 | Chiralpak AD | 15% isopropanol in heptane | 54 min |

-continued

| No | Name | Racemate example No | Chiral Column | Solvent | Retention time |
|----|------|---------------------|---------------|---------|----------------|
| 35 | (+)-2-Methylsulfanyl-N-[phenyl-(1-pyrrolidin-1-yl-cyclobutyl)-methyl]-4-trifluoromethyl-benzamide | 16 | Chiralpak AD | 15% isopropanol in heptane | 168 min |

The following examples were prepared according to the method in examples 1:

| No | Structure | Name | MS: m/e | Acid | Amine |
|----|-----------|------|---------|------|-------|
| 36 | 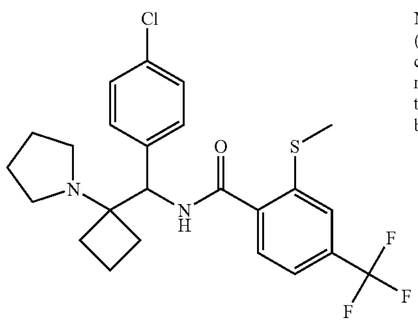 | N-[(4-Chloro-phenyl)-(1-pyrrolidin-1-yl-cyclobutyl)-methyl]-methylsulfanyl-4-trifluoromethyl-benzamide | 483.4 | 2-Methylsulfanyl-4-trifluoromethyl-benzoic acid (intermediate J) | C-(4-Fluoro-phenyl)-C-(1-pyrrolidin-1-yl-cyclobutyl)-methylamine (intermediate K) |
| 37 | 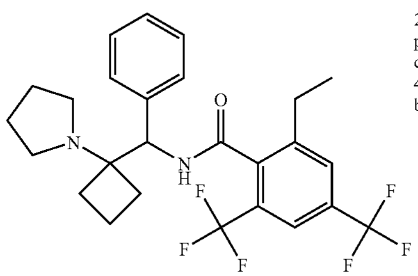 | 2-Ethyl-N-[phenyl)-(1-pyrrolidin-1-yl-cyclobutyl)-methyl]-2-4,6-bis-trifluoromethyl-benzamide | 499.3 | 2-Ethyl-4,6-bis-trifluoromethyl-benzoic acid (intermediate M) | C-Phenyl-C-(1-pyrrolidin-1-yl-cyclobutyl)-methylamine (intermediate G) |
| 38 | 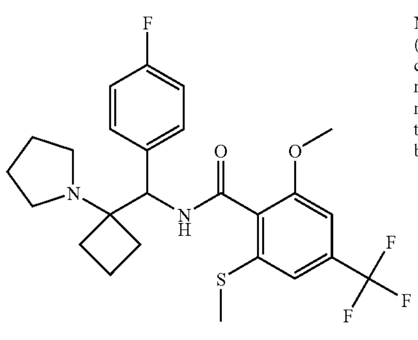 | N-[(4-Fluoro-phenyl)-(1-pyrrolidin-1-yl-cyclobutyl)-methyl]-2-methoxy-6-methylsulfanyl-4-trifluoromethyl-benzamide | 497.4 | 2-Methylsulfanyl-4,6-bis-trifluoromethyl-benzoic acid (CAS 896120-49-3) | C-(4-Fluoro-phenyl)-C-(1-pyrrolidin-1-yl-cyclobutyl)-methylamine (intermediate K) |
| 39 | 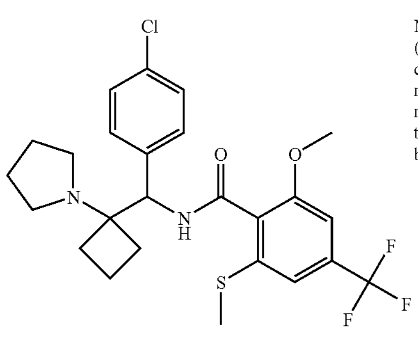 | N-[(4-Chloro-phenyl)-(1-pyrrolidin-1-yl-cyclobutyl)-methyl]-2-methoxy-6-methylsulfanyl-4-trifluoromethyl-benzamide | 513.4 | 2-Methylsulfanyl-4,6-bis-trifluoromethyl-benzoic acid (CAS 896120-49-3) | C-(4-Fluoro-phenyl)-C-(1-pyrrolidin-1-yl-cyclobutyl)-methylamine (intermediate K) |

-continued

| No | Structure | Name | MS: m/e | Acid | Amine |
|---|---|---|---|---|---|
| 40 | 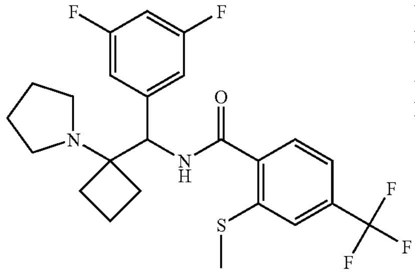 | N-[(3,5-Difluoro-phenyl)-(1-pyrrolidin-1-yl-cyclobutyl)-methyl]-2-methylsulfanyl-4-trifluoromethyl-benzamide | 485.3 | 2-Methylsulfanyl-4-trifluoromethyl-benzoic acid (intermediate J) | C-(3,5-Difluoro-phenyl)-C-(1-pyrrolidin-1-yl-cyclobutyl)-methylamine (intermediate N) |
| 41 | 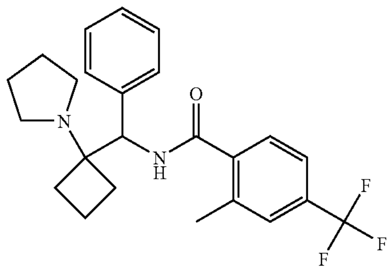 | 2-Methyl-N-[phenyl-(1-pyrrolidin-1-yl-cyclobutyl)-methyl]-4-trifluoromethyl-benzamide | 417.3 | 2-Methyl-4-trifluoromethyl-benzoic acid (CAS 23984-82-9) | C-Phenyl-C-(1-pyrrolidin-1-yl-cyclobutyl)-methylamine (intermediate G) |
| 42 | 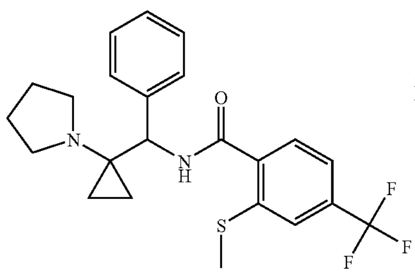 | 2-Methylsulfanyl-N-[phenyl-(1-pyrrolidin-1-yl-cyclopropyl)-methyl]-4-trifluoromethyl-benzamide | 435.3 | 2-Methylsulfanyl-4-trifluoromethyl-benzoic acid (intermediate J) | C-Phenyl-C-(1-pyrrolidin-1-yl-cyclopropyl)-methylamine (intermediate D) |
| 43 | 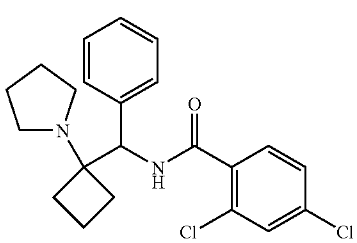 | 2,4-Dichloro-N-[phenyl-(1-pyrrolidin-1-yl-cyclobutyl)-methyl]-benzamide | 403.3 | 2,4-Dichlorobenzoic acid | C-Phenyl)-C-(1-pyrrolidin-1-yl-cyclobutyl)-methylamine (intermediate G) |
| 44 | 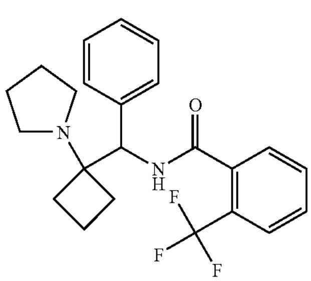 | N-[Phenyl-(1-pyrrolidin-1-yl-cyclobutyl)-methyl]-2-trifluoromethyl-benzamide | 403.3 | 2-(Trifluoroethyl)benzoic acid | C-Phenyl-C-(1-pyrrolidin-1-yl-cyclobutyl)-methylamine (intermediate G) |

-continued

| No | Structure | Name | MS: m/e | Acid | Amine |
|---|---|---|---|---|---|
| 45 | 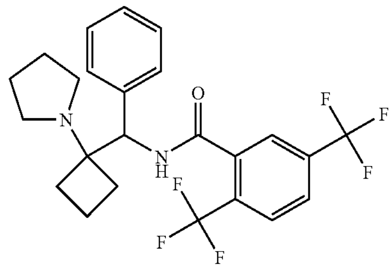 | N-[Phenyl-(1-pyrrolidin-1-yl-cyclobutyl)-methyl]-2,5-bis-trifluoromethyl-benzamide | 471.4 | 2,5-Bis(trifluoroethyl)benzoic acid | C-Phenyl-C-(1-pyrrolidin-1-yl-cyclobutyl)-methylamine (intermediate G) |
| 46 | 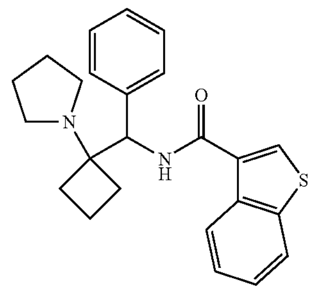 | Benzo[b]thiophene-3-carboxylic acid [phenyl-(1-pyrrolidin-1-yl-cyclobutyl)-methyl]-amide | 391.3 | 1-Benzothiophene-3-carboxylic acid | C-Phenyl-C-(1-pyrrolidin-1-yl-cyclobutyl)-methylamine (intermediate G) |
| 47 | 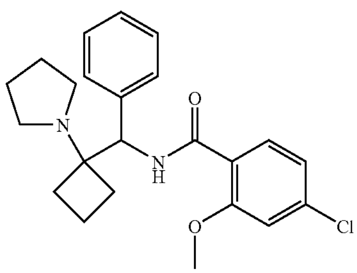 | 4-Chloro-2-methoxy-N-[phenyl-(1-pyrrolidin-1-yl-cyclobutyl)-methyl]-benzamide | 399.3 | 4-Chloro-2-methoxybenzoic acid | C-Phenyl-C-(1-pyrrolidin-1-yl-cyclobutyl)-methylamine (intermediate G) |
| 48 | 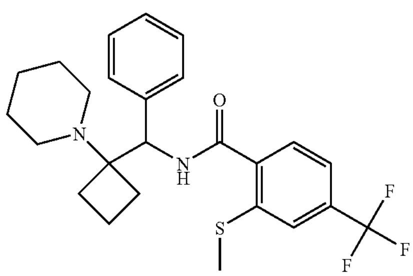 | 2-Methylsulfanyl-N-[phenyl-(1-piperidin-1-yl-cyclobutyl)-methyl]-4-trifluoromethyl-benzamide | 463.3 | 2-Methylsulfanyl-4-trifluoromethyl-benzoic acid (intermediate J) | C-Phenyl)-C-(1-piperidin-1-yl-cyclobutyl)-methylamine (intermediate P) |
| 49 | 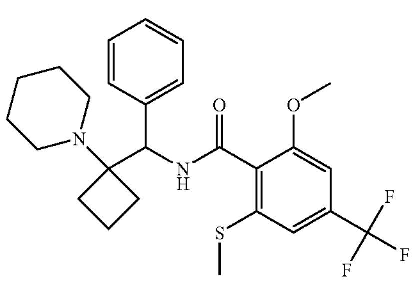 | 2-Methoxy-6-methylsulfanyl-N-[phenyl-(1-piperidin-1-yl-cyclobutyl)-methyl]-4-trifluoromethyl-benzamide | 493.3 | 2-Methylsulfanyl-4,6-bis-trifluoromethyl-benzoic acid (CAS 896120-49-3) | C-Phenyl)-C-(1-piperidin-1-yl-cyclobutyl)-methylamine (intermediate P) |

-continued

| No | Structure | Name | MS: m/e | Acid | Amine |
|---|---|---|---|---|---|
| 50 | 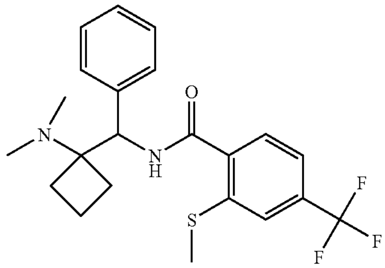 | N-[(1-Dimethylamino-cyclobutyl)-phenyl-methyl]-2-methylsulfanyl-4-trifluoromethyl-benzamide | 423.2 | 2-Methylsulfanyl-4-trifluoromethyl-benzoic acid intermediate J) | [1-(Amino-phenyl-methyl)-cyclobutyl]-dimethyl-amine (intermediate R) |
| 51 | 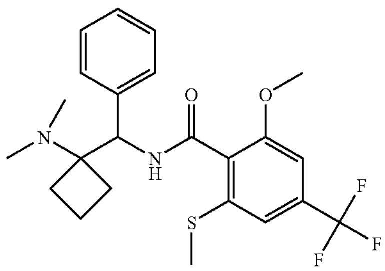 | N-[(1-Dimethylamino-cyclobutyl)-phenyl-methyl]-2-methoxy-6-methylsulfanyl-4-trifluoromethyl-benzamide | 453.3 | 2-Methylsulfanyl-4,6-bis-trifluoromethyl-benzoic acid (CAS 896120-49-3) | [1-(Amino-phenyl-methyl)-cyclobutyl]-dimethyl-amine (intermediate R) |
| 52 | 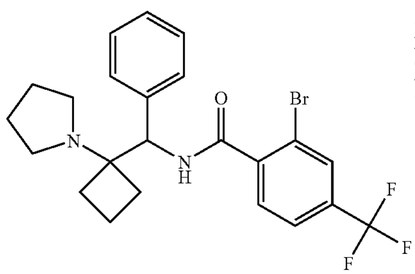 | 2-Bromo-N-[phenyl-(1-pyrrolidin-1-yl-cyclobutyl)-methyl]-4-trifluoromethyl-benzamide | 483.3 | 2-Bromo-4-trifluoromethyl benzoic acid (CAS 328-89-2) | C-Phenyl-C-(1-pyrrolidin-1-yl-cyclobutyl)-methylamine (intermediate G) |
| 53 | 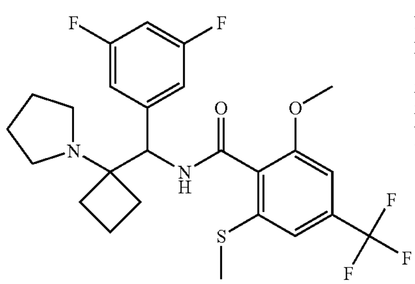 | N-[(3,5-Difluoro-phenyl-(1-pyrrolidin-1-yl-cyclobutyl)-methyl]-2-methoxy-6-methylsulfanyl-4-trifluoromethyl-benzamide | 515.3 | 2-Methylsulfanyl-4,6-bis-trifluoromethyl-benzoic acid (CAS 896120-49-3) | C-(3,5-Difluoro-phenyl)-C-(1-pyrrolidin-1-yl-cyclobutyl)-methylamine (intermediate N) |

The following examples were prepared according to the method in examples 1:

| Ex. | Structure | Name | MS: m/e | Acid | Amine |
|---|---|---|---|---|---|
| 54 | 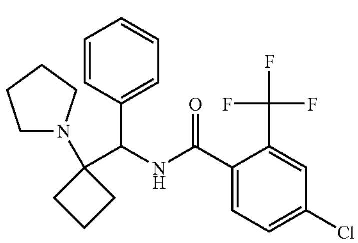 | 4-Chloro-N-phenyl-(1-pyrrolidin-1-yl-cyclobutyl)-methyl]-2-trifluoromethyl-benzamide | 437.2 | 4-Chloro-2-(trifluoromethyl) benzoic acid | C-Phenyl-C-(1-pyrrolidin-1-yl-cyclobutyl)-methylamine (intermediate G) |

-continued

| Ex. | Structure | Name | MS: m/e | Acid | Amine |
|---|---|---|---|---|---|
| 55 | 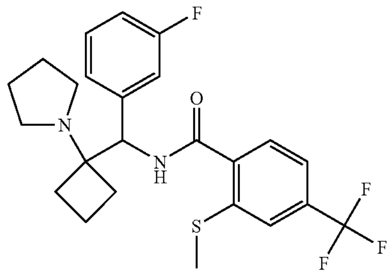 | N-[(3-Fluoro-phenyl)-(1-pyrrolidin-1-yl-cyclobutyl)-methyl]-2-methylsulfanyl-4-trifluoromethyl-benzamide | 467.3 | 2-Methylsulfanyl-4-trifluoromethyl-benzoic acid (intermediate J) | C-(3-Fluoro-phenyl)-C-(1-pyrrolidin-1-yl-cyclobutyl)-methylamine (intermediate S) |
| 56 | 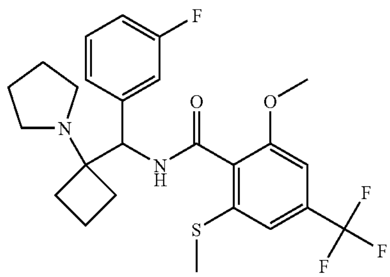 | N-[(3-Fluoro-phenyl)-(1-pyrrolidin-1-yl-cyclobutyl)-methyl]-2-methoxy-6-methylsulfanyl-4-trifluoromethyl-benzamide | 497.4 | 2-Methoxy-6-methylsulfanyl-4-trifluoromethyl-benzoic acid (intermediate H) | C-(3-Fluoro-phenyl)-C-(1-pyrrolidin-1-yl-cyclobutyl)-methylamine (intermediate S) |
| 57 | 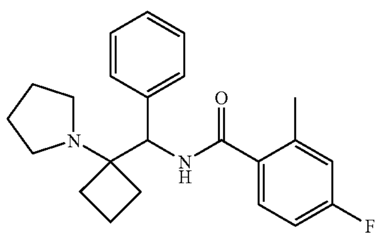 | 4-Fluoro-2-methyl-N-[phenyl-(1-pyrrolidin-1-yl-cyclobutyl)-methyl]-benzamide | 367.2 | 4-Fluoro-2-methylbenzoic acid | C-Phenyl-C-(1-pyrrolidin-1-yl-cyclobutyl)-methylamine (intermediate G) |
| 58 | 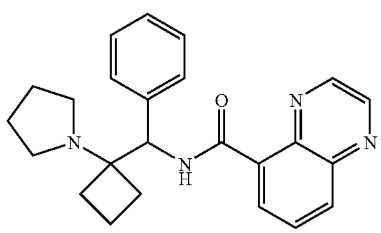 | Quinoxaline-5-carboxylic acid [phenyl-(1-pyrrolidin-1-yl-cyclobutyl)-methyl]-amide | 387.3 | Quinoxaline-5-carboxylic acid | C-Phenyl-C-(1-pyrrolidin-1-yl-cyclobutyl)-methylamine (intermediate G) |
| 59 | 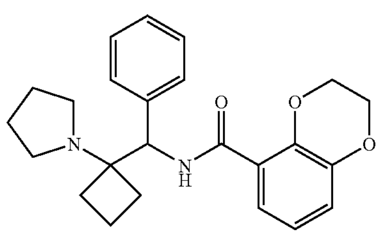 | 2,3-Dihydro-benzo[1,4]dioxine-5-carboxylic acid [phenyl-(1-pyrrolidin-1-yl-cyclobutyl)-methyl]-amide | 393.3 | 1,4-Benzodioxan-5-carboxylic acid | C-Phenyl-C-(1-pyrrolidin-1-yl-cyclobutyl)-methylamine (intermediate G) |
| 60 | 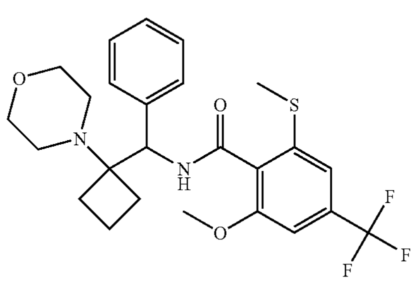 | 2-Methoxy-6-methylsulfanyl-N-[(1-morpholin-4-yl-cyclobutyl)-phenyl-methyl]-4-trifluoromethyl-benzamide | 495.4 | 2-Methoxy-6-Methylsulfanyl-4-trifluoromethyl-benzoic acid (intermediate H) | C-(1-Morpholin-4-yl-cyclobutyl)-C-phenyl-methylamine (intermediate U) |

-continued

| Ex. | Structure | Name | MS: m/e | Acid | Amine |
|---|---|---|---|---|---|
| 61 | 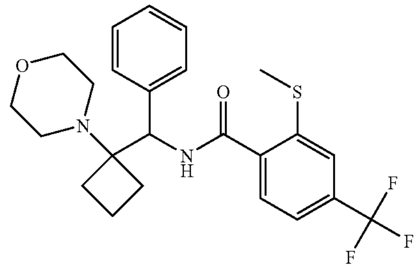 | 2-Methylsulfanyl-N-[(1-morpholin-4-yl-cyclobutyl)-phenyl-methyl]-4-trifluoromethyl-benzamide | 465.3 | 2-Methylsulfanyl-4-trifluoromethyl-benzoic acid (intermediate J) | C-(1-Morpholin-4-yl-cyclobutyl)-C-phenyl-methylamine (intermediate U) |
| 62 | 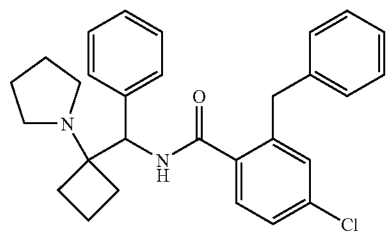 | 2-Benzyl-4-chloro-N-[phenyl-(1-pyrrolidin-1-yl-cyclobutyl)-methyl]-benzamide | 459.4 | 4-Chloro-2-(phenylmethyl)benzoic acid (CAS 81992-90-7) | C-Phenyl-C-(1-pyrrolidin-1-yl-cyclobutyl)-methylamine (intermediate G) |
| 63 | 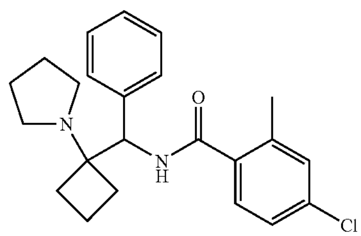 | 4-Chloro-2-methyl-N-[phenyl-(1-pyrrolidin-1-yl-cyclobutyl)-methyl]-benzamide | 383.2 | 4-Chloro-2-methylbenzoic acid | C-Phenyl-C-(1-pyrrolidin-1-yl-cyclobutyl)-methylamine (intermediate G) |
| 64 | 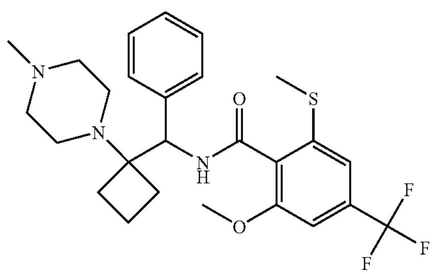 | 2-Methoxy-N-{[1-(4-methyl-piperazin-1-yl)-cyclobutyl]-phenyl-methyl}-6-methylsulfanyl-4-trifluoromethyl-benzamide | 508.3 | 2-Methoxy-6-methylsulfanyl-4-trifluoromethyl-benzoic acid (intermediate H) | C-[1-(4-Methyl-piperazin-1-yl)-cyclobutyl]-C-phenyl-methylamine (intermediate W) |
| 65 | 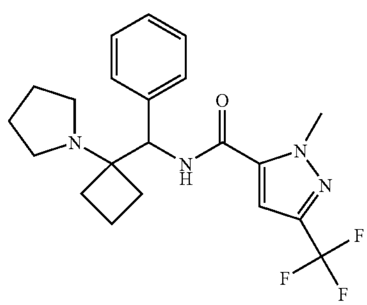 | 2-Methyl-5-trifluoromethyl-2H-pyrazole-3-carboxylic acid [phenyl-(1-pyrrolidin-1-yl-cyclobutyl)-methyl]-amide | 407.3 | 2-Methyl-5-trifluoromethyl-2H-pyrazole-3-carboxylic acid | C-Phenyl-C-(1-pyrrolidin-1-yl-cyclobutyl)-methylamine (intermediate G) |
| 66 | 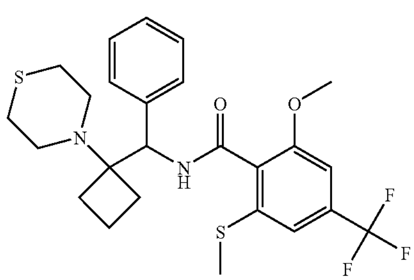 | 2-Methoxy-6-methylsulfanyl-N-[phenyl-(1-thiomorpholin-4-yl-cyclobutyl)-methyl]-4-trifluoromethyl-benzamide | 511.3 | 2-Methoxy-6-Methylsulfanyl-4-trifluoromethyl-benzoic acid (intermediate H) | C-Phenyl-C-(1-thiomorpholin-4-yl-cyclobutyl)-methylamine (intermediate Y) |

-continued

| Ex. | Structure | Name | MS: m/e | Acid | Amine |
|---|---|---|---|---|---|
| 67 | 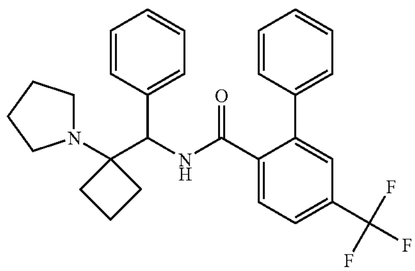 | 5-Trifluoromethyl-biphenyl-2-carboxylic acid [phenyl-(1-pyrrolidin-1-yl-cyclobutyl)-methyl]-amide | 479.3 | 5-Trifluoromethyl-biphenyl-2-carboxylic acid (intermediate Z) | C-Phenyl-C-(1-pyrrolidin-1-yl-cyclobutyl)-methylamine (intermediate G) |
| 68 | 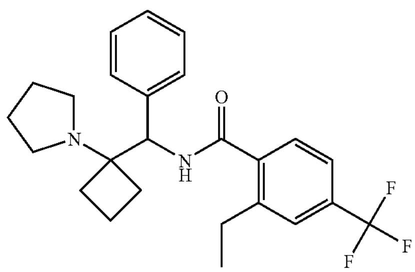 | 2-Ethyl-N-[phenyl-(1-pyrrolidin-1-yl-cyclobutyl)-methyl]-4-trifluoromethyl-benzamide | 431.3 | 2-Ethyl-4-(trifluoromethyl)-benzoic acid (CAS 854531-63-8) | C-Phenyl-C-(1-pyrrolidin-1-yl-cyclobutyl)-methylamine (intermediate G) |
| 69 | 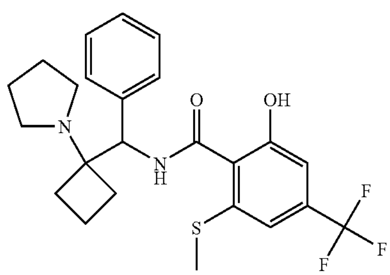 | 2-Hydroxy-6-methylsulfanyl-N-[phenyl-(1-pyrrolidin-1-yl-cyclobutyl)-methyl]-4-trifluoromethyl-benzamide | 465.3 | 2-Hydroxy-6-methylsulfanyl-4-trifluoromethyl-benzoic acid (intermediate AA) | C-Phenyl-C-(1-pyrrolidin-1-yl-cyclobutyl)-methylamine (intermediate G) |
| 70 | 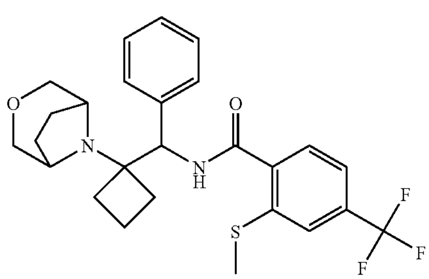 | (rac)-2-Methylsulfanyl-N-{[1-(3-oxa-8-aza-bicyclo[3.2.1]oct-8-yl)-cyclobutyl]-phenyl-methyl}-4-trifluoromethyl-benzamide | 491.2 | 2-Methylsulfanyl-4-trifluoromethyl-benzoic acid (intermediate J) | C-[1-(3-Oxa-8-aza-bicyclo[3.2.1]oct-8-yl)-cyclobutyl]-C-phenyl-methylamine (intermediate AC) |
| 71 | 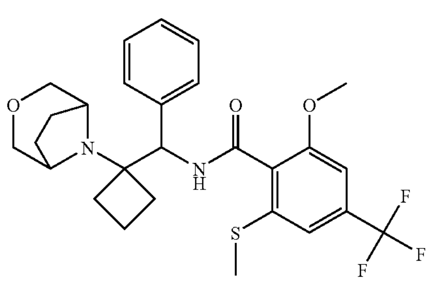 | (rac)-2-Methoxy-6-methylsulfanyl-N-{[1-(3-oxa-8-aza-bicyclo[3.2.1]oct-8-yl)-cyclobutyl]-phenyl-methyl}-4-trifluoromethyl-benzamide | 521.3 | 2-Methoxy-6-Methylsulfanyl-4-trifluoromethyl-benzoic acid (intermediate H) | C-[1-(3-Oxa-8-aza-bicyclo[3.2.1]oct-8-yl)-cyclobutyl]-C-phenyl-methylamine (intermediate AC) |

-continued

| Ex. | Structure | Name | MS: m/e | Acid | Amine |
|---|---|---|---|---|---|
| 72 | 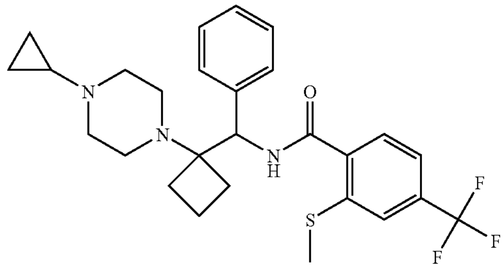 | N-{[1-(4-Cyclopropyl-piperazin-1-yl)-cyclobutyl]-phenyl-methyl}-2-methylsulfanyl-4-trifluoromethyl-benzamide | 504.2 | 2-Methylsulfanyl-4-trifluoromethyl-benzoic acid (intermediate J) | C-[1-(4-Cyclopropyl-piperazin-1-yl)-cyclobutyl]-C-phenyl-methylamine (intermediate AE) |
| 73 | 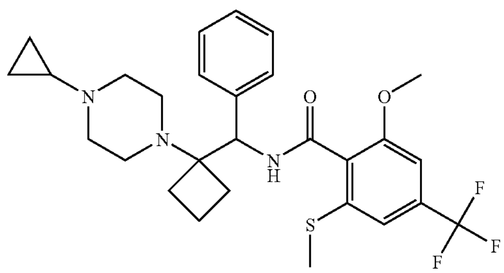 | N-{[1-(4-Cyclopropyl-piperazin-1-yl)-cyclobutyl]-phenyl-methyl}-2-methoxy-6-methylsulfanyl-4-trifluoromethyl-benzamide | 534.3 | 2-Methoxy-6-Methylsulfanyl-4-trifluoromethyl-benzoic acid (intermediate H) | C-[1-(4-Cyclopropyl-piperazin-1-yl)-cyclobutyl]-C-phenyl-methylamine (intermediate AE) |
| 74 | 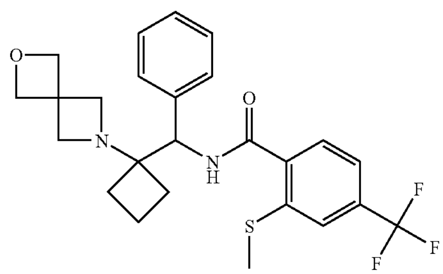 | 2-Methylsulfanyl-N-{[1-(2-oxa-6-aza-spiro[3.3]hept-6-yl)-cyclobutyl]-phenyl-methyl}-4-trifluoromethyl-benzamide | 477.2 | 2-Methylsulfanyl-4-trifluoromethyl-benzoic acid (intermediate J) | C-[1-(2-Oxa-6-aza-spiro[3.3]hept-6-yl)-cyclobutyl]-C-phenyl-methylamine (intermediate AG) |
| 75 | 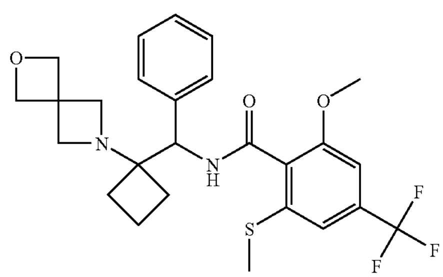 | 2-Methoxy-6-methylsulfanyl-N-{[1-(2-oxa-6-aza-spiro[3.3]hept-6-yl)-cyclobutyl]-phenyl-methyl}-4-trifluoromethyl-benzamide | 507.2 | 2-Methoxy-6-methylsulfanyl-4-trifluoromethyl-benzoic acid (intermediate H) | C-[1-(2-Oxa-6-aza-spiro[3.3]hept-6-yl)-cyclobutyl]-C-phenyl-methylamine (intermediate AG) |

The invention claimed is:

1. A compound of formula I

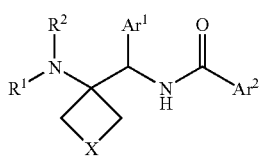

I wherein

R$^1$ and R$^2$ are each independently lower alkyl, or together with the N-atom to which they are attached form a heterocyclic group selected from pyrrolidine, piperidine, piperazine, 4-methyl-piperazine, 4-cyclopropyl-piperazine, thiomorpholine, morpholine, 1-(3-oxa-8-aza-bicyclo[3.2.1]oct-8-yl and 1-(2-oxa-6-aza-spiro[3.3]hept-6-yl;

X is a bond, —CH$_2$— or —O—;

Ar$^1$ is aryl or heteroaryl, each of which is unsubstituted or substituted by one or two substituents selected from halogen, lower alkyl, lower alkoxy, and lower alkyl substituted by halogen;

Ar$^2$ is aryl or heteroaryl, each of which is unsubstituted or substituted by one, two or three substituents selected from halogen, lower alkyl, lower alkoxy, hydroxy, lower alkyl substituted by halogen, lower alkoxy substituted by halogen, S-lower alkyl, benzyl and phenyl;

or a pharmaceutically acceptable acid addition salt, a racemic mixtures or their corresponding enantiomer and/or optical isomer thereof.

2. The compound of claim 1, wherein X is a bond.

3. The compound of claim 2, selected from the group consisting of
2-methoxy-N-[phenyl-(1-pyrrolidin-1-yl-cyclopropyl)-methyl]-4,6-bis-trifluoromethyl-benzamide;
4-fluoro-2-methoxy-6-methylsulfanyl-N-[phenyl-(1-pyrrolidin-1-yl-cyclopropyl)-methyl]-benzamide;
2-methyl-N-[phenyl-(1-pyrrolidin-1-yl-cyclopropyl)-methyl]-4,6-bis-trifluoromethyl-benzamide;
2-methylsulfanyl-N-[phenyl-(1-pyrrolidin-1-yl-cyclopropyl)-methyl]4,6-bis-trifluoromethyl-benzamide;
2-methoxy-6-methylsulfanyl-N-[phenyl-(1-pyrrolidin-1-yl-cyclopropyl)-methyl]-benzamide;
2-methoxy-6-methylsulfanyl-N-[phenyl-(1-pyrrolidin-1-yl-cyclopropyl)-methyl]-4-trifluoromethyl-benzamide;
(−)-2-methoxy-N-[phenyl-(1-pyrrolidin-1-yl-cyclopropyl)-methyl]-4,6-bis-trifluoromethyl-benzamide;
(−)-4-fluoro-2-methoxy-6-methylsulfanyl-N-[phenyl-(1-pyrrolidin-1-yl-cyclopropyl)-methyl]-benzamide;
(−)-2-methylsulfanyl-N-[phenyl-(1-pyrrolidin-1-yl-cyclopropyl)-methyl]-4,6-bis-trifluoromethyl-benzamide; and
2-methylsulfanyl-N-[phenyl-(1-pyrrolidin-1-yl-cyclopropyl)-methyl]-4-trifluoromethyl-benzamide.

4. The compound of claim 1, wherein X is —CH$_2$—.

5. The compound of claim 4, selected from the group consisting of
2-methylsulfanyl-N-[phenyl-(1-pyrrolidin-1-yl-cyclobutyl)-methyl]-4,6-bis-trifluoromethyl-benzamide;
4-fluoro-2-methoxy-6-methylsulfanyl-N-[phenyl-(1-pyrrolidin-1-yl-cyclobutyl)-methyl]-benzamide;
2-methoxy-6-methylsulfanyl-N-[phenyl-(1-pyrrolidin-1-yl-cyclobutyl)-methyl]-4-trifluoromethyl-benzamide;
2-methylsulfanyl-N-[phenyl-(1-pyrrolidin-1-yl-cyclobutyl)-methyl]-6-trifluoromethyl-benzamide;
2-methoxy-N-[phenyl-(1-pyrrolidin-1-yl-cyclobutyl)-methyl]-4,6-bis-trifluoromethyl-benzamide;
N-[phenyl-(1-pyrrolidin-1-yl-cyclobutyl)-methyl]-2,4-bis-trifluoromethyl-benzamide;
2-methylsulfanyl-N-[phenyl-(1-pyrrolidin-1-yl-cyclobutyl)-methyl]-4-trifluoromethyl-benzamide;
2-methoxy-N-[phenyl-(1-pyrrolidin-1-yl cyclobutyl)-methyl]-4-trifluoromethyl-benzamide;
N-[(4-fluoro-phenyl)-(1-pyrrolidin-1-yl-cyclobutyl)-methyl]-2-methylsulfanyl-4-trifluoromethyl-benzamide;
(+)-2-methylsulfanyl-N-[phenyl-(1-pyrrolidin-1-yl-cyclobutyl)-methyl]-4,6-bis-trifluoromethyl-benzamide; and
(−)-2-methylsulfanyl-N-[phenyl-(1-pyrrolidin-1-yl-cyclobutyl)-methyl]-4,6-bis-trifluoromethyl-benzamide.

6. The compound of claim 4, selected from the group consisting of
(+)-2-methoxy-6-methylsulfanyl-N-[phenyl-(1-pyrrolidin-1-yl-cyclobutyl)-methyl]-4-trifluoromethyl-benzamide;
(+)-2-methoxy-6-methylsulfanyl-N-[phenyl-(1-pyrrolidin-1-yl-cyclobutyl)-methyl]-4-trifluoromethyl-benzamide;
(+)-2-methylsulfanyl-N-[phenyl-(1-pyrrolidin-1-yl-cyclobutyl)-methyl]-4-trifluoromethyl-benzamide;
N-[(4-chloro-phenyl)-(1-pyrrolidin-1-yl-cyclobutyl)-methyl]-2-methylsulfanyl-4-trifluoromethyl-benzamide;
2-ethyl-N-[phenyl-(1-pyrrolidin-1-yl-cyclobutyl)-methyl]-4,6-bis-trifluoromethyl-benzamide;
N-[(4-fluoro-phenyl)-(1-pyrrolidin-1-yl-cyclobutyl)-methyl]-2-methoxy-6-methylsulfanyl-4-trifluoromethyl-benzamide;
N-[(4-chloro-phenyl)-(1-pyrrolidin-1-yl-cyclobutyl)-methyl]-2-methoxy-6-methylsulfanyl-4-trifluoromethyl-benzamide;
N-[(3,5-difluoro-phenyl)-(1-pyrrolidin-1-yl-cyclobutyl)-methyl]-2-methylsulfanyl-4-trifluoromethyl-benzamide;
2-methyl-N-[phenyl-(1-pyrrolidin-1-yl-cyclobutyl)-methyl]-4-trifluoromethyl-benzamide
2,4-Dichloro-N-[phenyl-(1-pyrrolidin-1-yl-cyclobutyl)-methyl]-benzamide;
N-[phenyl-(1-pyrrolidin-1-yl-cyclobutyl)-methyl]-2-trifluoromethyl-benzamide;
4-chloro-2-methoxy-N-[phenyl-(1-pyrrolidin-1-yl-cyclobutyl)-methyl]-benzamide; and
2-methylsulfanyl-N-[phenyl-(1-piperidin-1-yl-cyclobutyl)-methyl]-4-trifluoromethyl-benzamide.

7. The compound of claim 4, selected from the group consisting of
2-methoxy-6-methylsulfanyl-N-[phenyl-(1-piperidin-1-yl-cyclobutyl)-methyl]-4-trifluoromethyl-benzamide;
N-[(1-dimethylamino-cyclobutyl)-phenyl-methyl]-2-methylsulfanyl-4-trifluoromethyl-benzamide;
N-[(1-dimethylamino-cyclobutyl)-phenyl-methyl]-2-methoxy-6-methylsulfanyl-4-trifluoromethyl-benzamide;
2-bromo-N-[phenyl-(1-pyrrolidin-1-yl-cyclobutyl)-methyl]-4-trifluoromethyl-benzamide;
N-[(3,5-difluoro-phenyl)-(1-pyrrolidin-1-yl-cyclobutyl)-methyl]-2-methoxy-6-methylsulfanyl-4-trifluoromethyl-benzamide;
4-chloro-N-[phenyl-(1-pyrrolidin-1-yl-cyclobutyl)-methyl]-2-trifluoromethyl-benzamide;
N-[(3-fluoro-phenyl)-(1-pyrrolidin-1-yl-cyclobutyl)-methyl]-2-methylsulfanyl-4-trifluoromethyl-benzamide;
N-[(3-fluoro-phenyl)-(1-pyrrolidin-1-yl-cyclobutyl)-methyl]-2-methoxy-6-methylsulfanyl-4-trifluoromethyl-benzamide;
4-fluoro-2-methyl-N-[phenyl-(1-pyrrolidin-1-yl-cyclobutyl)-methyl]-benzamide;
2-methoxy-6-methylsulfanyl-N-[(1-morpholin-4-yl-cyclobutyl)-phenyl-methyl]-4-trifluoromethyl-benzamide; and
4-chloro-2-methyl-N-[phenyl-(1-pyrrolidin-1-yl-cyclobutyl)-methyl]-benzamide.

8. The compound of claim 4, selected from the group consisting of
2-methoxy-6-methylsulfanyl-N-[phenyl-(1-thiomorpholin-4-yl-cyclobutyl)-methyl]-4-trifluoromethyl-benzamide;
5-trifluoromethyl-biphenyl-2-carboxylic acid [phenyl-(1-pyrrolidin-1-yl-cyclobutyl)-methyl]-amide;
2-ethyl-N-[phenyl-(1-pyrrolidin-1-yl-cyclobutyl)-methyl]-4-trifluoromethyl-benzamide;
2-hydroxy-6-methylsulfanyl-N-[phenyl-(1-pyrrolidin-1-yl-cyclobutyl)-methyl]-4-trifluoromethyl-benzamide;
(rac)-2-methoxy-6-methylsulfanyl-N-{1-(3-oxa-8-aza-bicyclo[3.2.1]oct-8-yl)-cyclobutyl]-phenyl-methyl}-4-trifluoromethyl-benzamide;
N-{[1-(4-cyclopropyl-piperazin-1-yl)-cyclobutyl]-phenyl-methyl}-2-methylsulfanyl-4-trifluoromethyl-benzamide;
N-{[1-(4-cyclopropyl-piperazin-1-yl)-cyclobutyl]-phenyl-methyl}-2-methoxy-6-methylsulfanyl-4-trifluoromethyl-benzamide;
2-methylsulfanyl-N-{[1-(2-oxa-6-aza-spiro[3.3]hept-6-yl)-cyclobutyl]-phenyl-methyl}-4-trifluoromethyl-benzamide; and 2-methoxy-6-methylsulfanyl-N-{[1-(2-oxa-6-aza-spiro[3.3]hept-6-yl)-cyclobutyl]-phenyl-methyl}-4-trifluoromethyl-benzamide.

9. The compound of claim 1, wherein X is —O—.

10. The compound of claim 9, selected from the group consisting of 2-methoxy-N-[phenyl-(3-pyrrolidin-1-yl-oxetan-3-yl)-methyl]-4,6-bis-trifluoromethyl-benzamide;
4-fluoro-2-methoxy-6-methylsulfanyl-N-[phenyl-(3-pyrrolidin-1-yl-oxetan-3-yl)-methyl]-benzamide;
2-methylsulfanyl-N-[phenyl-(3-pyrrolidin-1-yl-oxetan-3-yl)-methyl]-4,6-bis-trifluoromethyl-benzamide;
2-methoxy-6-methylsulfanyl-N-[phenyl-(3-pyrrolidin-1-yl-oxetan-3-yl)-methyl]-4-trifluoromethyl-benzamide;
2-methylsulfanyl-N-[phenyl-(3-pyrrolidin-1-yl-oxetan-3-yl)-methyl]-4-trifluoromethyl-benzamide;
(−)-2-methoxy-N-[phenyl-(3-pyrrolidin-1-yl-oxetan-3-yl)-methyl]-4,6-bis-trifluoromethyl-benzamide; and
(−)-4-fluoro-2-methoxy-6-methylsulfanyl-N-[phenyl-(3-pyrrolidin-1-yl-oxetan-3-yl)-methyl]-benzamide.

11. A pharmaceutical composition comprising a therapeutically effective amount of a compound of formula I

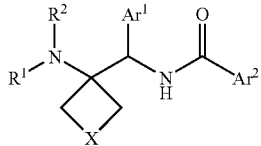

wherein $R^1$ and $R^2$ are each independently lower alkyl, or together with the N-atom to which they are attached form a heterocyclic group selected from pyrrolidine, piperidine, piperazine, 4-methyl-piperazine, 4-cyclopropyl-piperazine, thiomorpholine, morpholine, 1-(3-oxa-8-aza-bicyclo[3.2.1]oct-8-yl and 1-(2-oxa-6-aza-spiro[3.3]hept-6-yl;

X is a bond, —CH$_2$— or —O—;

$Ar^1$ is aryl or heteroaryl, each of which is unsubstituted or substituted by one or two substituents selected from halogen, lower alkyl, lower alkoxy, and lower alkyl substituted by halogen;

$Ar^2$ is aryl or heteroaryl, each of which is unsubstituted or substituted by one, two or three substituents selected from halogen, lower alkyl, lower alkoxy, hydroxy, lower alkyl substituted by halogen, lower alkoxy substituted by halogen, S-lower alkyl, benzyl and phenyl;

or a pharmaceutically acceptable acid addition salt, a racemic mixture, or their corresponding enantiomer and/or optical isomer thereof.

\* \* \* \* \*